(12) United States Patent
Yi et al.

(10) Patent No.: US 8,927,120 B2
(45) Date of Patent: Jan. 6, 2015

(54) HETEROCYCLIC COMPOUND AND ORGANIC LIGHT-EMITTING DEVICE INCLUDING THE SAME

(75) Inventors: Jeoung-In Yi, Yongin (KR); Seung-Gak Yang, Yongin (KR); Hee-Yeon Kim, Yongin (KR); Jae-Yong Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 301 days.

(21) Appl. No.: 13/480,251

(22) Filed: May 24, 2012

(65) Prior Publication Data

US 2012/0326138 A1    Dec. 27, 2012

(30) Foreign Application Priority Data

Jun. 22, 2011 (KR) .................. 10-2011-0060808

(51) Int. Cl.
*H01L 51/54* (2006.01)
*C07D 487/04* (2006.01)
*H01L 51/00* (2006.01)
*H01L 51/50* (2006.01)

(52) U.S. Cl.
CPC .......... *H01L 51/0072* (2013.01); *C07D 487/04* (2013.01); *H01L 51/5072* (2013.01); *Y10S 428/917* (2013.01)
USPC ........... 428/690; 428/917; 313/504; 313/506; 548/418

(58) Field of Classification Search
CPC ............. C07D 487/04; H01L 51/0072; H01L 51/5072
See application file for complete search history.

(56) References Cited

U.S. PATENT DOCUMENTS 6,559,256 B2    5/2003    Holmes et al.
7,597,955 B2   10/2009    Takiguchi et al.
(Continued)

FOREIGN PATENT DOCUMENTS

JP    2007-049055    2/2007
JP    2008-133225    6/2008
(Continued)

*Primary Examiner* — Dawn L. Garrett
(74) *Attorney, Agent, or Firm* — Robert E. Bushnell, Esq.

(57) ABSTRACT

A heterocyclic compound represented by Formula 1 or Formula 2 below, an organic light-emitting device including the heterocyclic compound, and a flat display device including the organic light-emitting device:

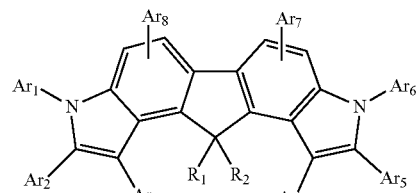

Formula 1

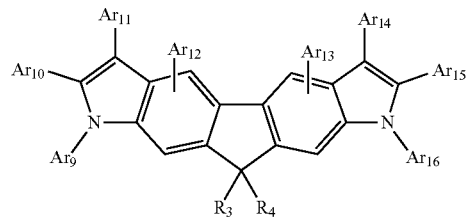

Formula 2 wherein $Ar_1$ to $Ar_{16}$, and $R_1$ to $R_4$ are defined as in the specification.

19 Claims, 1 Drawing Sheet

(56) References Cited

U.S. PATENT DOCUMENTS

| | | |
|---|---|---|
| 7,846,559 B2 | 12/2010 | Hwang et al. |
| 7,875,368 B2 | 1/2011 | Ohrui et al. |
| 2010/0108995 A1 | 5/2010 | Yagi et al. |
| 2011/0031483 A1 | 2/2011 | Kwak et al. |
| 2011/0049488 A1 | 3/2011 | Kim et al. |
| 2012/0068170 A1* | 3/2012 | Pflumm et al. .................. 257/40 |

FOREIGN PATENT DOCUMENTS

| | | |
|---|---|---|
| KR | 1020060085471 A | 7/2006 |
| KR | 10-2010-0014605 A | 2/2010 |
| KR | 10-2011-0016031 A | 2/2011 |
| WO | 2005/051046 A | 6/2005 |

* cited by examiner

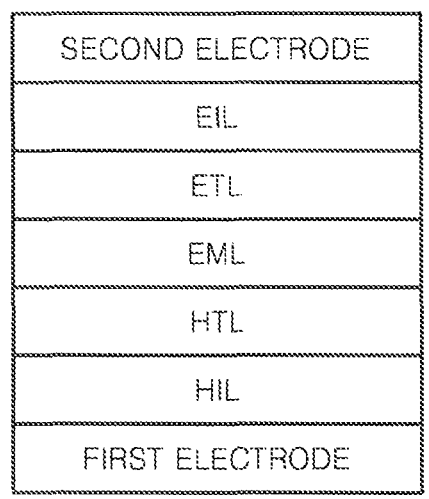

HETEROCYCLIC COMPOUND AND ORGANIC LIGHT-EMITTING DEVICE INCLUDING THE SAME

CLAIM OF PRIORITY

This application makes reference to, incorporates the same herein, and claims all benefits accruing under 35 U.S.C. §119 from an application for HETEROCYCLIC COMPOUND AND ORGANIC LIGHT-EMITTING DEVICE INCLUDING THE SAME earlier filed in the Korean Intellectual Property Office on 22 Jun. 2011 and there duly assigned Serial No. 10-2011-0060808.

BACKGROUND OF THE INVENTION

1. Field of the Invention

The present invention relates to a heterocyclic compound represented by Formula 1 or Formula 2 and an organic light-emitting device including the heterocyclic compound and a flat panel display device including the organic light-emitting device.

2. Description of the Related Art

Light-emitting devices are self-emission type display devices and have a wide viewing angle, a high contrast ratio, and a short response time. Due to these characteristics, light-emitting devices are drawing more attention. Such light-emitting devices can be roughly classified into inorganic light-emitting devices that include emission layers containing inorganic compounds, and organic light-emitting devices that include emission layers containing organic compounds. Specifically, organic light-emitting devices have higher luminance, lower driving voltages, and shorter response times than inorganic light-emitting devices, and can render multicolored displays. Thus, many researches into such organic light-emitting devices have been conducted. Typically, an organic light-emitting device has a stack structure including an anode, a cathode and an organic emission layer interposed therebetween. However, a hole injection layer and/or a hole transport layer may be further stacked between the anode and the organic emission layer, and/or an electron transport layer may be further stacked between the organic emission layer and the cathode. In other words, an organic light-emitting device may have a stack structure of anode/hole transport layer/organic emission layer/cathode or a stack structure of anode/hole transport layer/organic emission layer/electron transport layer/cathode.

As a material for forming the organic emission layer, naphthalene derivatives can be used. However, organic light-emitting devices including such materials may not have satisfactory life span, efficiency, and power consumption characteristics, thereby improvement in this regard still being necessary.

SUMMARY OF THE INVENTION

The present invention provides a novel heterocyclic compound having improved electrical characteristics, improved charge transporting capabilities or improved light-emission capabilities.

The present invention provides an organic light-emitting device including the heterocyclic compound.

The present invention provides a flat panel display device including the organic light-emitting device.

According to an aspect of the present invention, there is provided a heterocyclic compound represented by Formula 1 or Formula 2 below:

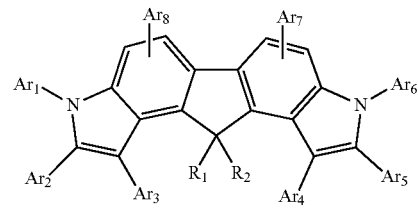

Formula 1 wherein, in Formula 1, $R_1$ and $R_2$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a halogen atom, a cyano group, a nitro group, a hydroxyl group, or a carboxyl group; and $Ar_1$ to $Ar_8$ are each independently a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_4$-$C_{60}$ heteroaryl group, a substituted or unsubstituted $C_4$-$C_{60}$ heteroaryl group, or a substituted or unsubstituted $C_6$-$C_{60}$ condensed polycyclic group, and

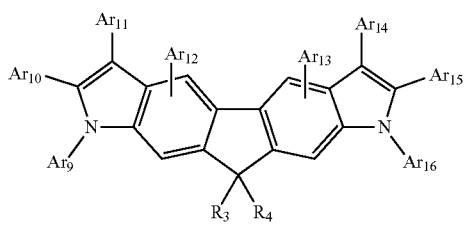

Formula 2 wherein, in Formula 2, $R_3$ and $R_4$ are each independently a hydrogen atom, a deuterium atom, a substituted or =substituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a halogen atom, a cyano group, a nitro group, a hydroxyl group, or a carboxyl group; and $Ar_9$ to $Ar_{16}$ are each independently a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_4$-$C_{60}$ heteroaryl group, a substituted or unsubstituted $C_4$-$C_{60}$ heteroaryl group, or a substituted or unsubstituted $C_6$-$C_{60}$ condensed polycyclic group.

In some embodiments, $R_1$ to $R_4$ in Formulae 1 and 2 may be each independently selected from the group consisting of a hydrogen atom, a deuterium atom, a halogen atom, a cyano group, and a substituted or unsubstituted $C_1$-$C_{20}$ alkyl group.

In some embodiments, $Ar_1$ to $Ar_{16}$ may be each independently selected from among groups represented by Formulae 2a to 2f below:

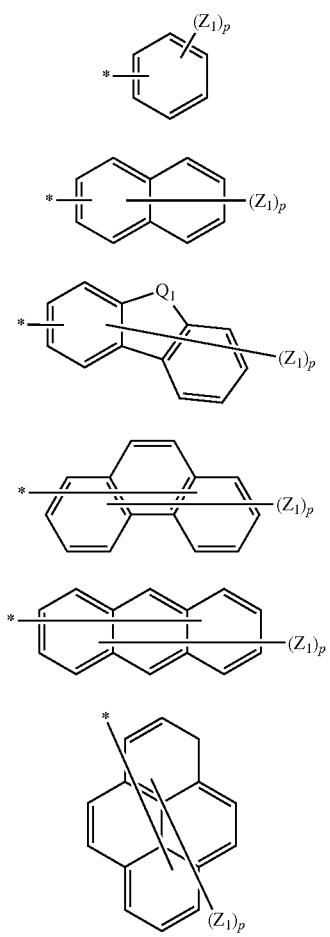

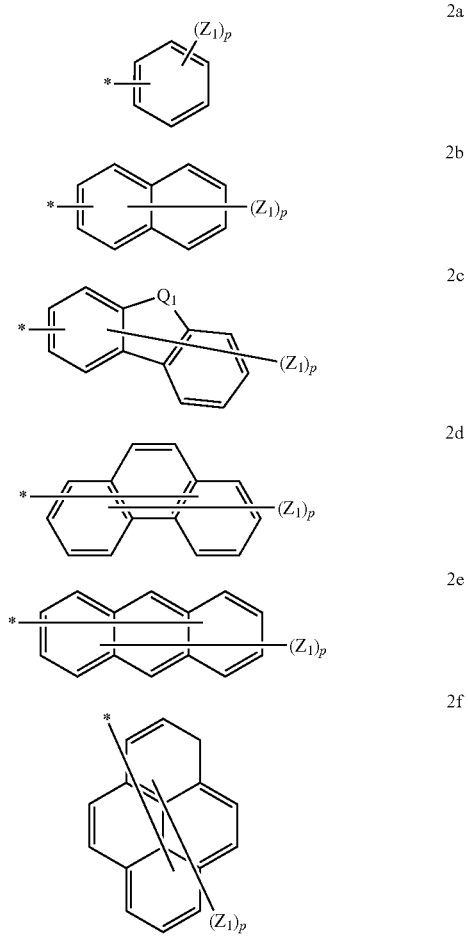

wherein, in Formulae 2a to 2f, $Q_1$ is a linking group represented by —C($R_5$)($R_6$)—, —N(R)—, —S—, or —O—; $Z_1$, $R_5$, $R_6$, and $R_7$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 12; and * indicates a binding site.

In some embodiments, $R_1$ to $R_4$ in Formulae 1 and 2 may be each independently selected from the group consisting of a hydrogen atom, a deuterium atom, a cyano group, a halogen atom, and a substituted or unsubstituted $C_1$-$C_{20}$ alkyl group; and $Ar_9$ to $Ar_{16}$ be each independently a substituted or unsubstituted $C_5$-$C_{30}$ aryl group, a substituted or unsubstituted $C_4$-$C_{30}$ heteroaryl group, or a substituted or unsubstituted $C_6$-$C_{30}$ condensed polycyclic group.

In some embodiments, $R_1$ to $R_4$ in Formulae 1 and 2 may be substituted or unsubstituted $C_1$-$C_{20}$ alkyl groups; and $Ar_7$, $Ar_8$, $Ar_{12}$, and $Ar_{13}$ may be hydrogen atoms.

In some embodiments, $R_1$ to $R_4$ in Formulae 1 and 2 may be methyl groups, $Ar_7$, $Ar_8$, $Ar_{12}$, and $Ar_{13}$ may be hydrogen atoms; and $Ar_1$ to $Ar_6$, $Ar_9$ to $Ar_{11}$, and $Ar_{14}$ to $Ar_{16}$ may be each independently selected from among groups represented by Formulae 2a to 2f:

wherein, in Formulae 2a to 2f, $Q_1$ is a linking group represented by —C($R_5$)($R_6$)—, —N($R_7$)—, —S—, or —O—; $Z_1$, $R_5$, $R_6$, and $R_7$ may be each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 12; and * indicates a binding site.

In some embodiments, the compound of Formula 1 or Formula 2 may include one of the compounds below:

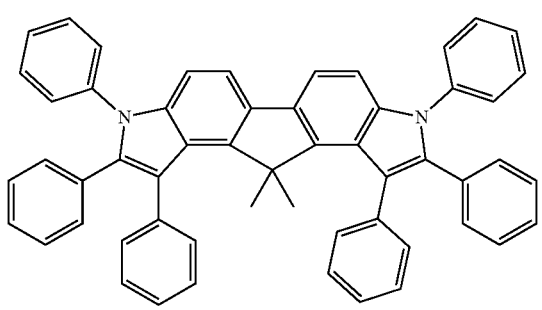

1

-continued

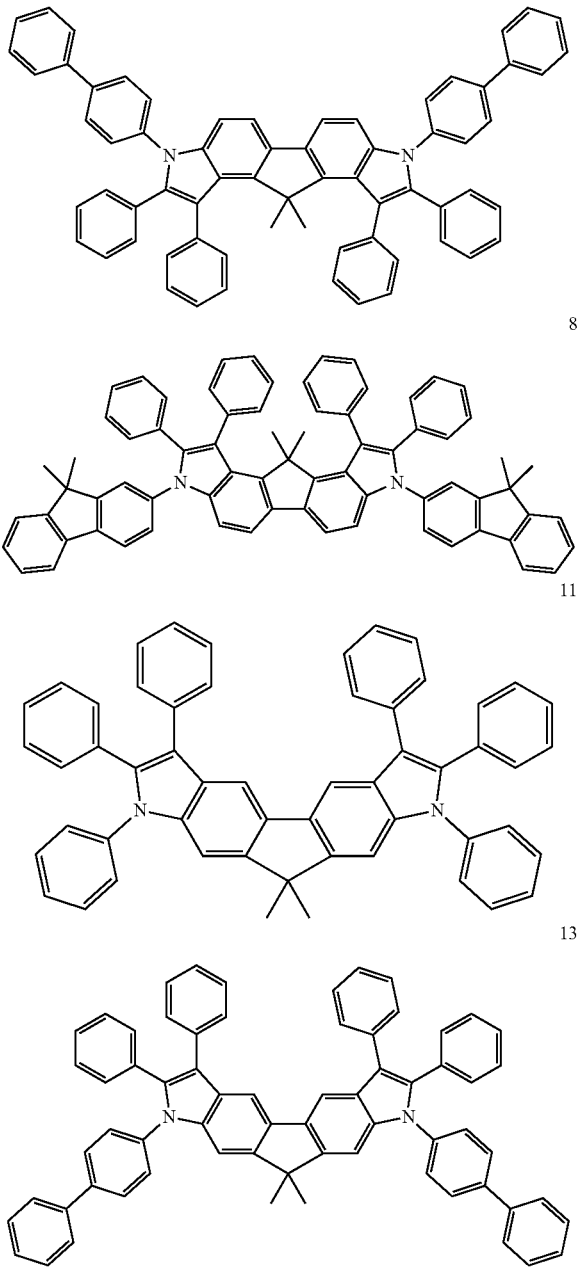

According to another aspect of the present invention, there is provided an organic light-emitting device including: a first electrode; a second electrode; and an organic layer formed between the first electrode and the second electrode, wherein the organic layer may include a first layer including the heterocyclic compound of Formula 1 or Formula 2 described above.

In some embodiments, the first layer may include an electron injection layer, an electron transport layer, or a single layer having hole injecting and transporting capabilities.

In some embodiments the first layer may include an emission layer and a hole transport layer, the electron transport layer may include the compound of Formula 1 or Formula 2, and the emission layer may include an anthracene compound, an arylamine compound, or a styryl compound.

In some embodiments the first layer may include an emission layer and a hole transport layer, the electron transport layer may include the compound of Formula 1 or Formula 2, and the emission layer may include red, green, blue, and white emission layers one of which includes a phosphorescent compound.

In some embodiments the organic layer may further include a hole injection layer, a hole transport layer, a functional layer having both hole injection and hole transport capabilities, an emission layer, a hole blocking layer, an electron transport layer, an electron injection layer, or a combination of at least two thereof.

In some embodiments at least one of the hole injection layer, the hole transport layer, and the functional layer having hole injection and hole transport capabilities may further include a charge generating material.

In some embodiments the electron transport layer may include an electron transporting organic material and a metal-containing material.

In some embodiments the metal-containing material may include a lithium (Li) complex.

In some embodiments the organic light emitting device may include a plurality of organic layers, at least one layer of which may be formed using the heterocyclic compound of Formula 1 or Formula 2 by a wet process.

According to another aspect of the present invention, there is provided a flat panel display device including the organic light-emitting device described above, wherein the first electrode of the organic light-emitting device may be electrically connected to a source electrode or a drain electrode of a thin-film transistor.

BRIEF DESCRIPTION OF THE DRAWINGS

A more complete appreciation of the present invention, and many of the attendant advantages thereof, will be readily apparent as the present invention becomes better understood by reference to the following detailed description when considered in conjunction with the accompanying drawings in which like reference symbols indicate the same or similar components, wherein:

FIG. 1 illustrates a structure of an organic light-emitting device according to an embodiment of the present invention.

DETAILED DESCRIPTION OF THE INVENTION

Heteroaromatic compounds such as oxadiazoles are known as materials for forming an electron transport layer of an organic light-emitting device (OLED). However, there has been a need for such existing OLEDs to improve their driving voltage, current density, efficiency and lifetime characteristics.

As materials for forming an electron transport layer, there have been reported compounds having a molecular core of 9,9-diphenylfluorene structure bound with pyrrole, indole, carbazole or the like. However, such compounds fail to provide satisfactory driving voltage, current density, efficiency and lifetime characteristics.

There also has been reported a compound with at least one indole group and at least one carbazole group in its molecule. However, this compound provides unsatisfactory driving voltage, current density, efficiency and lifetime characteristics.

The present invention will now be described more fully with reference to the accompanying drawings, in which exemplary embodiments of the invention are shown.

An aspect of the present invention provides a heterocyclic compound represented by Formula 1 below.

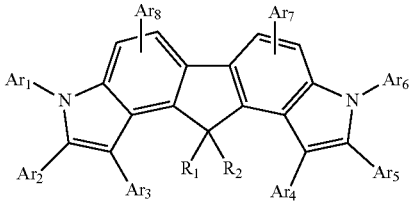

Formula 1

In Formula 1, $R_1$ and $R_2$ may be each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a halogen atom, a cyano group, a nitro group, a hydroxyl group, or a carboxyl group; and $Ar_1$ to $Ar_8$ may be each independently a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_4$-$C_{60}$ heteroaryl group, a substituted or unsubstituted $C_4$-$C_{60}$ heteroaryl group, or a substituted or unsubstituted $C_6$-$C_{60}$ condensed polycyclic group.

An aspect of the present invention provides a heterocyclic compound represented by Formula 2 below.

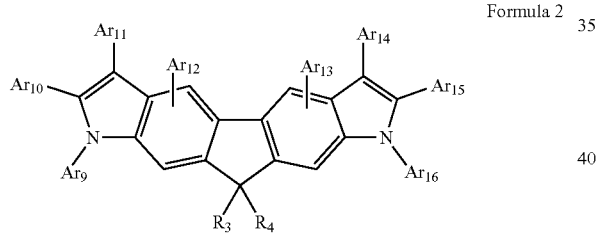

Formula 2

In Formula 2, $R_3$ and $R_4$ may be each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a halogen atom, a cyano group, a nitro group, a hydroxyl group, or a carboxyl group; and $Ar_9$ to $Ar_{16}$ may be each independently a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_4$-$C_{60}$ heteroaryl group, a substituted or unsubstituted $C_4$-$C_{60}$ heteroaryl group, or a substituted or unsubstituted $C_6$-$C_{60}$ condensed polycyclic group.

In some embodiments the heterocyclic compound of Formula 1 and/or the heterocyclic compound of Formula 2 may be used as a light-emitting material, an electron-transporting material or an electron-injecting material. The heterocyclic compound of Formula 1 and the heterocyclic compound of Formula 2, each having a heterocyclic group in the molecules thereof, may have a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments.

An organic light-emitting device manufactured using the heterocyclic compound of Formula 1 or Formula 2 has high durability when stored or operated.

Substituents in the heterocyclic compounds of Formulae 1 and 2 will now be described in detail.

In some embodiments, $R_1$ to $R_4$ in Formulae 1 and 2 may be each independently selected from the group consisting of a hydrogen atom, a deuterium atom, a halogen atom, a cyano group, and a substituted or unsubstituted $C_1$-$C_{20}$ alkyl group.

In some embodiments, $Ar_1$ to $Ar_{16}$ may be each independently selected from among groups represented by Formulae 2a to 2f below:

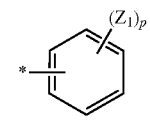

2a

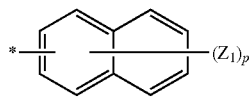

2b

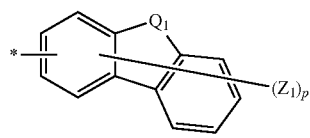

2c

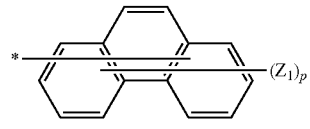

2d

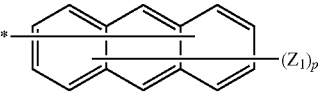

2e

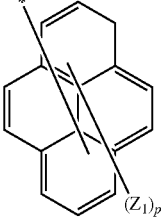

2f

In Formulae 2a to 2f, $Q_1$ may be a linking group represented by —C($R_5$)($R_6$)—, —N($R_7$)—, —S—, or —O—; $Z_1$, $R_5$, $R_6$, and $R_7$ may be each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 12; and * indicates a binding site.

In some embodiments, $R_1$ to $R_4$ in Formulae 1 and 2 may be each independently selected from the group consisting of a hydrogen atom, a deuterium atom, a cyano group, a halogen atom, and a substituted or unsubstituted $C_1$-$C_{20}$ alkyl group, and $Ar_9$ to $Ar_{16}$ may be each independently a substituted or unsubstituted $C_5$-$C_{30}$ aryl group, a substituted or unsubstituted $C_4$-$C_{30}$ heteroaryl group, or a substituted or unsubstituted $C_6$-$C_{30}$ condensed polycyclic group.

In some embodiments, $R_1$ to $R_4$ in Formulae 1 and 2 may be substituted or unsubstituted $C_1$-$C_{20}$alkyl groups, and $Ar_7$, $Ar_8$, $Ar_{12}$, and $Ar_{13}$ may be hydrogen atoms.

In some embodiments, $R_1$ to $R_4$ in Formulae 1 and 2 may be methyl groups; and $Ar_7$, $Ar_8$, $Ar_{12}$, and $Ar_{13}$ may be hydrogen atoms; and $Ar_1$ to $Ar_6$, $Ar_9$ to $Ar_{11}$, and $Ar_{14}$ to $Ar_{16}$ may be each independently selected from among groups represented by Formulae 2a to 2f.

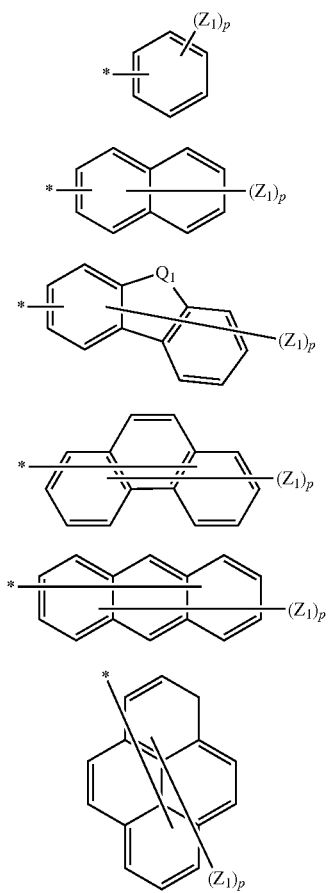

In Formulae 2a to 2f, $Q_1$ may be a linking group represented by —C($R_5$)($R_6$)—, —N($R_7$)—, —S—, or —O—; $Z_1$, $R_5$, $R_6$, and $R_7$ may be each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 12; and * indicates a binding site.

Hereinafter, substituents described with reference to Formulae 1 and 2 will now be described in detail. In this regard, the numbers of carbons in substituents are presented only for illustrative purposes and do not limit the characteristics of the substituents.

The unsubstituted $C_1$-$C_{60}$ alkyl group used herein may be linear or branched. Examples of the unsubstituted $C_1$-$C_{60}$ alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom in the unsubstituted $C_1$-$C_{60}$ alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsaturated alkyl groups having at least one carbon-carbon double bond in the center or at a terminal of the alkyl group. Examples of the unsubstituted $C_2$-$C_{60}$ alkenyl group include an ethenyl group, a propenyl group, a butenyl group, and the like. At least one hydrogen atom in the unsubstituted $C_2$-$C_{60}$ alkenyl group may be substituted with a substituent described above in conjunction with the unsubstituted $C_1$-$C_{60}$ alkyl group.

The unsubstituted $C_2$-$C_{60}$ alkynyl group indicates an alkyl group having at least one carbon-carbon triple bond in the center or at a terminal of the alkyl group. Examples of the unsubstituted $C_2$-$C_{20}$ alkynyl group include acetylene, propylene, phenylacetylene, naphthylacetylene, isopropylacetylene, t-butylacetylene, diphenylacetylene, and the like. At least me hydrogen atom in the unsubstituted $C_2$-$C_{60}$ alkynyl group may be substituted with a substituent described above in conjunction with the unsubstituted $C_1$-$C_{60}$ alkyl group.

The unsubstituted $C_3$-$C_{60}$ cycloalkyl group indicates a $C_3$-$C_{60}$ cyclic alkyl group wherein at least one hydrogen atom in the unsubstituted $C_3$-$C_{60}$ cycloalkyl group may be substituted with a substituent described above in conduction with the unsubstituted $C_1$-$C_{60}$ alkyl group.

The unsubstituted $C_1$-$C_{60}$ alkoxy group indicates a group having a structure of —OA wherein A is an unsubstituted $C_1$-$C_{60}$ alkyl group as described above. Non-limiting examples of the unsubstituted $C_1$-$C_{60}$ alkoxy group include a methoxy group, an ethoxy group, a propoxy group, an isopropyloxy group, a butoxy group, and a pentoxy group. At least one hydrogen atom in the unsubstituted $C_1$-$C_{60}$ alkoxy group may be substituted with a substituent such as those described above in conjunction with the unsubstituted $C_1$-$C_{60}$ alkyl group.

The unsubstituted $C_5$-$C_{60}$ aryl group indicates a carbocyclic aromatic system containing at least one ring. At least two rings in the unsubstituted $C_5$-$C_{60}$ aryl group may be fused to each other or linked to each other by a single bond. The term 'aryl' refers to an aromatic system, such as phenyl, naphthyl, or anthracenyl. At least one hydrogen atom in the unsubstituted $C_5$-$C_{60}$ aryl group may be substituted with a substituent described above in conjunction with the unsubstituted $C_1$-$C_{60}$ alkyl group.

Examples of the substituted or unsubstituted $C_5$-$C_{60}$ aryl group include, but are not limited to, a phenyl group, a $C_1$-$C_{10}$ alkylphenyl group (for example, ethylphenyl group), a halophenyl group (for example, o-, m-, and p-fluorophenyl group, dichlorophenyl group), a cyanophenyl group, a dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, an o-, m-, and p-toryl group, an o-, m-, and p-cumenyl group, a meshyl group, a phenoxyphenyl group, a (α,α-dimethylbenzene)phenyl group, (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaplithyl group (for example, methylnaphthyi group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenyiene group, a pyrenyl group, a chrycenyl group, an ethyl-cluysenyl group, a picenyl group, a petylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_4$-$C_{60}$ heteroaryl group used herein includes one, two or three hetero atoms selected from N, O, P and S. At least two rings may be fused to each other or linked to each other by a single bond. Examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the unsubstituted $C_4$-$C_{60}$ heteroaryl group may be substituted with a substituent described above in conjunction with the unsubstituted $C_1$-$C_{60}$ alkyl group.

The unsubstituted $C_5$-$C_{60}$ aryloxy group is a group represented by —$OA_1$ wherein $A_1$ may be a $C_5$-$C_{60}$ aryl group. An example of the unsubstituted $C_5$-$C_{60}$ aryloxy group is a phenoxy group. At least one hydrogen atom in the unsubstituted $C_5$-$C_{60}$ aryloxy group may be substituted with a substituent described above in conjunction with the unsubstituted $C_1$-$C_{60}$ alkyl group.

The unsubstituted $C_5$-$C_{60}$ arylthio group is represented by -$SA_1$ where $A_1$ may be a $C_5$-$C_{60}$ aryl group. Non-limiting examples of the unsubstituted $C_5$-$C_{60}$ arylthio group include a benzenethio group and a naphthylthio group. At least one hydrogen atom in the unsubstituted $C_5$-$C_{60}$ arylthio group may be substituted with a substituent described above in conjunction with the unsubstituted $C_1$-$C_{60}$ alkyl group.

The unsubstituted $C_6$-$C_{60}$ condensed polycyclic group used herein refers to a substituent including at least two rings wherein at least one aromatic ring and/or at least one non-aromatic ring are fused to each other.

Examples of the heterocyclic compound represented by Formula 1 or Formula 2 include Compounds 1 to 20 presented below. However, the compounds represented by Formula 1 or Formula 2 are not limited thereto.

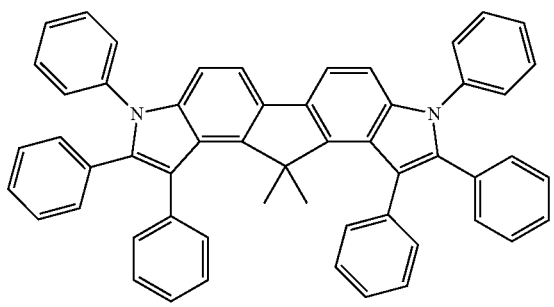

1

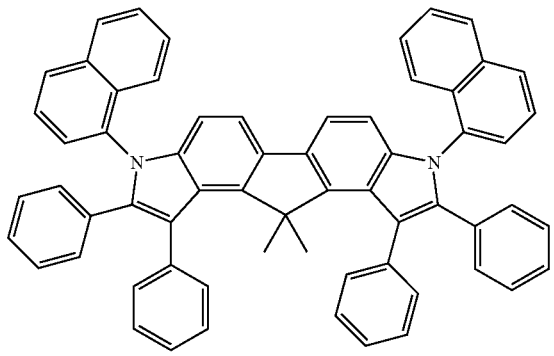

2

3
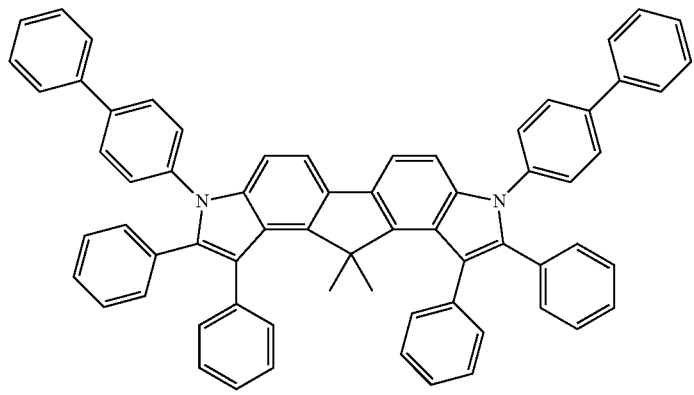
4
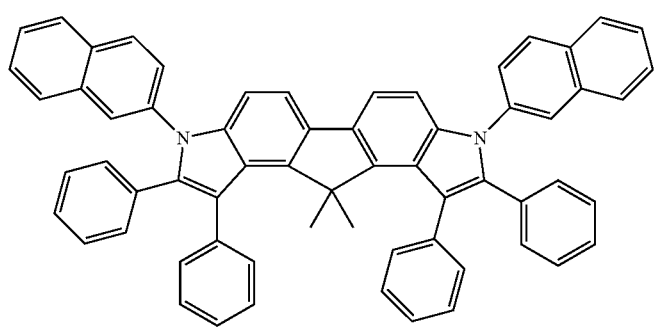
5
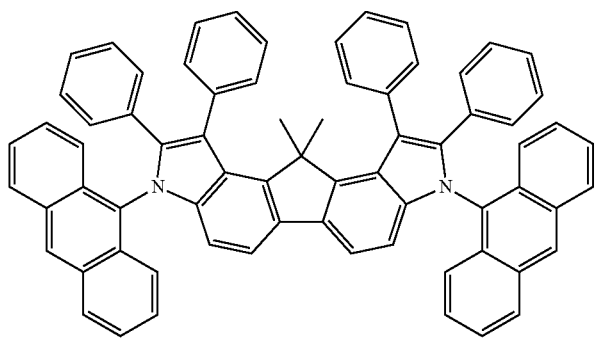
6
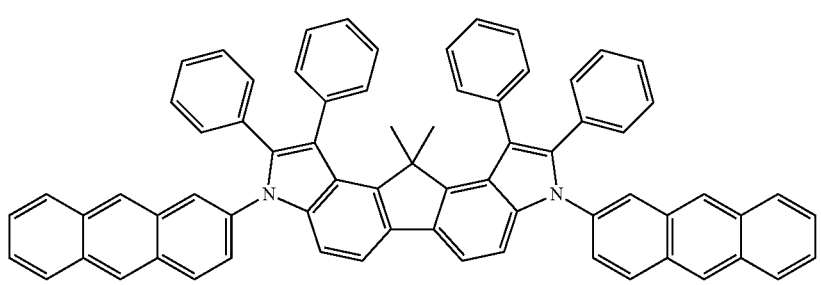

7
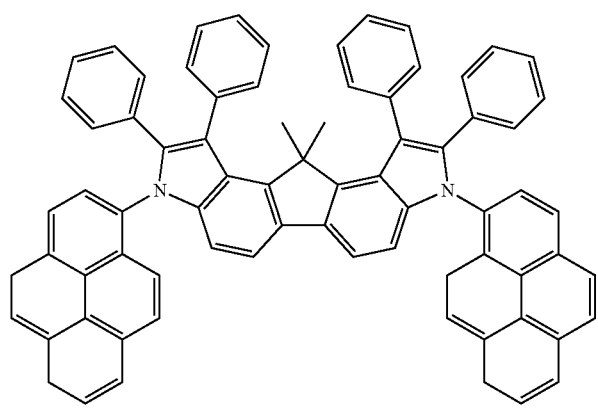
8
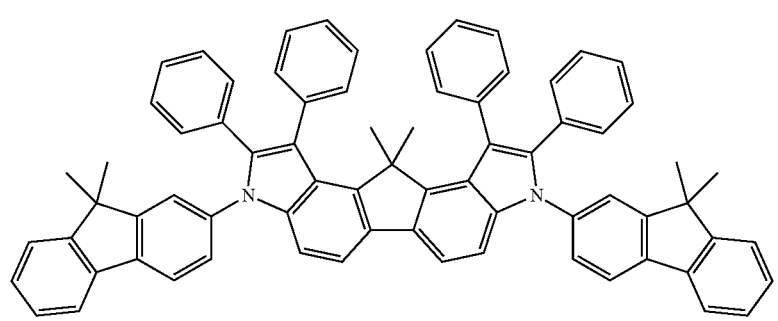
9
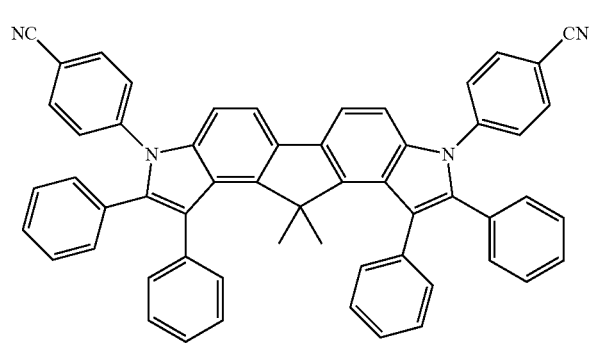
10
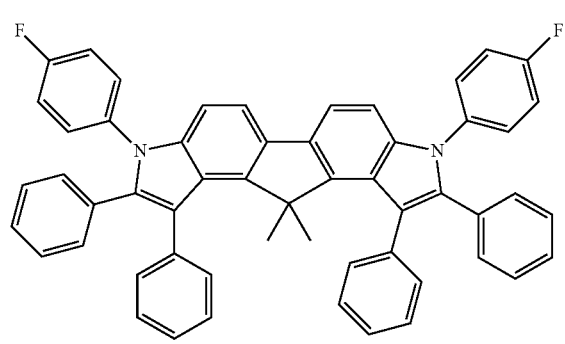

11
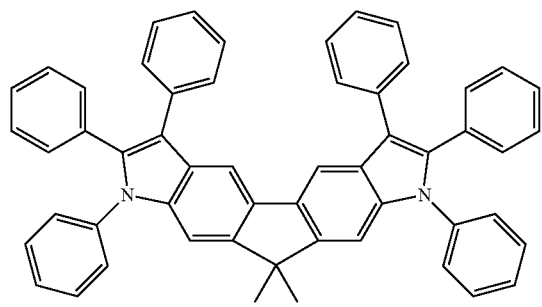
12
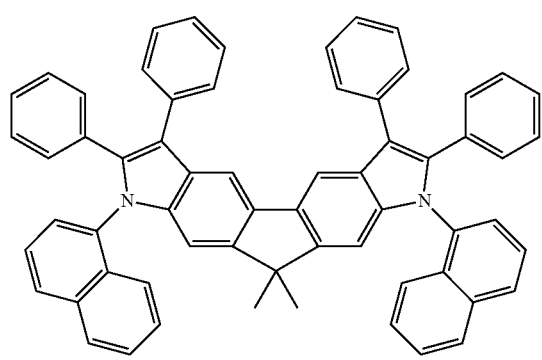
13
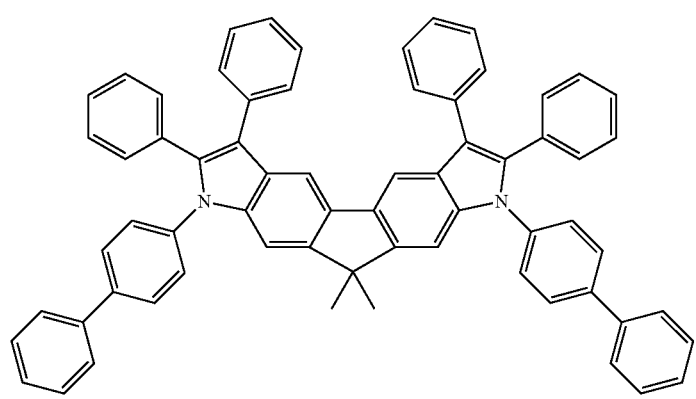
14
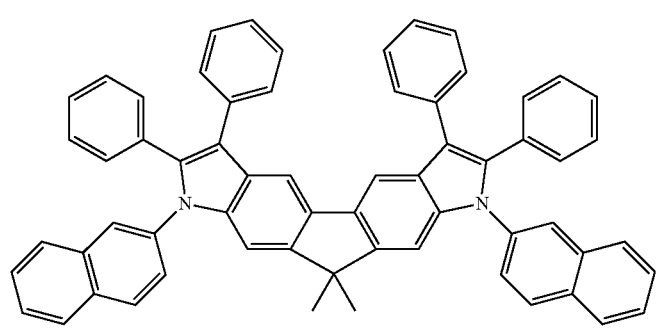

15
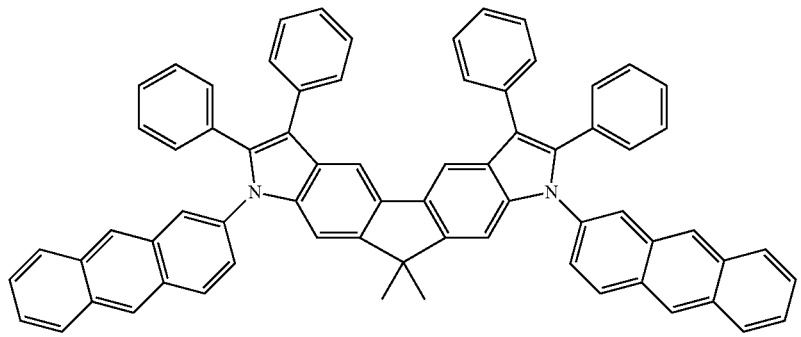
16
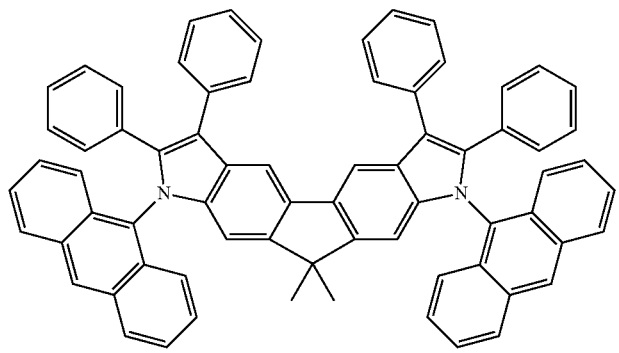
17
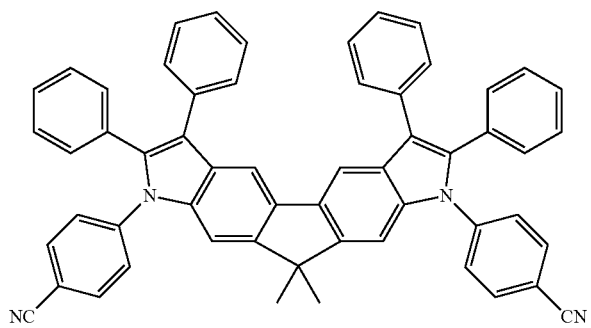
18
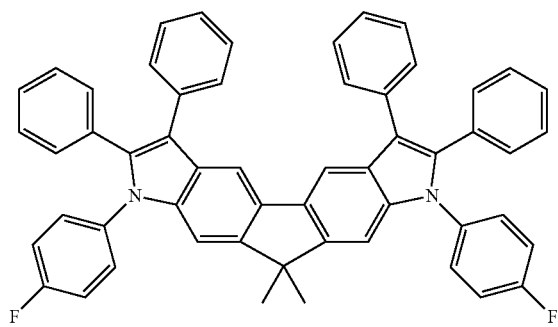

19

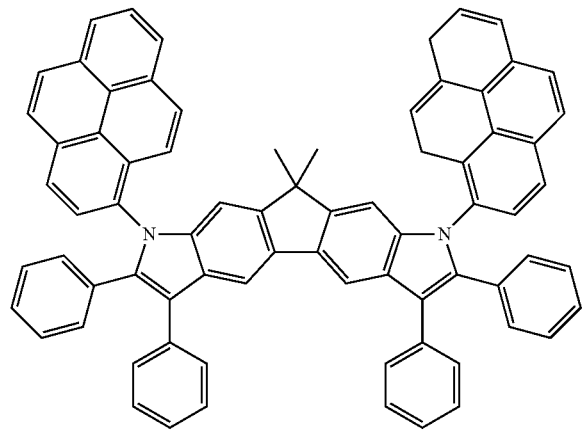

20

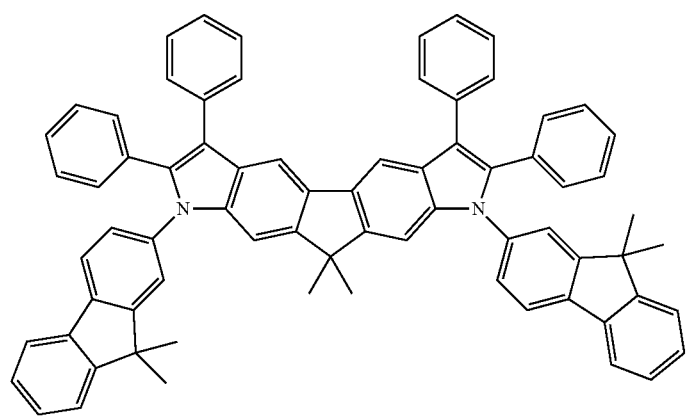

According to an embodiment, an organic light-emitting device includes a first electrode, a second electrode, and an organic layer formed between the first electrode and the second electrode, the organic layer including the heterocyclic compound of Formula 1 or Formula 2 described above.

In some embodiments, the organic layer including a layer including the heterocyclic compound of Formula 1 or Formula 2 described above and the layer may be an electron injection layer, an electron transport layer, or a single layer being able to both inject and transport holes.

In some embodiments, the organic layer of the organic light-emitting device may include an emission layer and an electron transport layer. When the electron transport layer includes the heterocyclic compound of Formula 1 or Formula 2, the emission layer may include an anthracene compound, an arylamine compound, or a styryl compound.

In addition, at least one hydrogen atom in the anthracene compound, the arylamine compound or the styryl compound may be substituted with a substituent described above in conjunction with the unsubstituted $C_1$-$C_{60}$ alkyl group. The arylamine refers to a $C_5$-$C_{60}$ arylamine group.

In some embodiments, the organic layer of the organic light-emitting device may include an emission layer and an electron transport layer. When the electron transport layer include the heterocyclic compound of Formula 1 or Formula 2, a red emission layer, a green emission layer, a blue emission layer or a white emission layer of the emission layer may include a phosphorescent compound.

In some embodiments, the organic layer of the organic light-emitting device may further include, but are not limited to, a hole injection layer, a hole transport layer, a functional layer having both hole injection and hole transport capabilities, an emission layer, a hole blocking layer, an electron transport layer, an electron injection layer, or a combination of at least two of them thereof. At least one of the hole injection layer, the hole transport layer, and the functional layer having both hole injection and hole transport capabilities may further include a charge generating material for improved layer conductivity, in addition to the heterocyclic compound of Formula 1 or Formula 2 described above, a widely-known hole injection material, and a widely-known hole transport material.

The charge generating material may include, for example, a p-dopant. Non-limiting examples of the p-dopant include quinone derivatives such as tetraeyanoquinonedimethane (TCNQ), 2,3,5,6-tetrafluoro-tetracyano-1,4-berizoquinortedimethane (F4TCNQ), and the like; metal oxides such as tungsten oxide, molybdenum oxide, and the like; and cyano-containing compounds such as Compound 100 below.

Compound 100

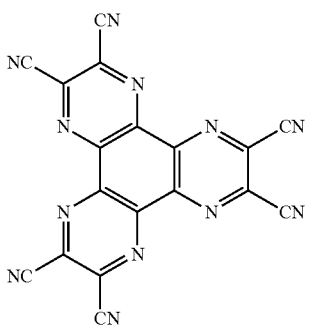

When one of the hole injection layer, the hole transport layer, and the functional layer having both hole injection and hole transport capabilities further includes a charge generating material, the charge generating material may be, but not limited to, uniformly dispersed or nonuniformly distributed in the layer.

In some embodiments, the electron transport layer of the organic light-emitting device may further include an electron-transporting organic compound and a metal-containing compound. Non-limiting examples of the electron-transporting organic compound include 9,10-di(naphthalen-2-yl)arithracene (ADN), and anthracene-based compounds, such as Compounds 101 and 102 below.

Compound 101

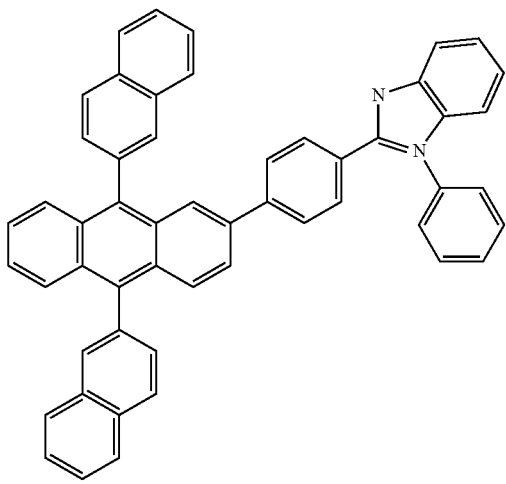

Compound 102

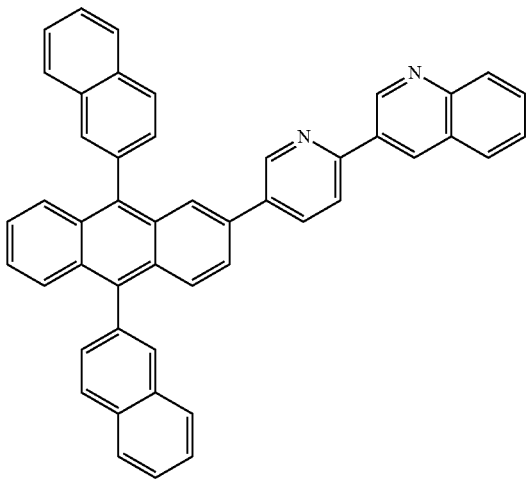

The metal-containing compound may include a lithium (Li) complex. Non-limiting examples of the Li complex include lithium quinolate (LiQ), Compound 103 below, and the like:

Compound 103

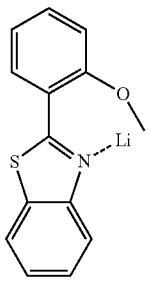

The first electrode may be an anode, and the second electrode may be a cathode, but the reverse is also possible.

In some embodiments, the organic light-emitting device may have a first electrode/a hole injection layer/an emission layer/a second electrode structure, a first electrode/a hole injection layer/a hole transport layer/an emission layer/an electron transport layer/a second electrode structure, or a first electrode/a hole injection layer/a hole transport layer/an emission layer/an electron transport layer/an electron injection layer/a second electrode structure. In some other embodiments, the organic light-emitting device may have a first electrode/a single layer having both hole injection and hole transport capabilities/an emission layer/an election transport layer/a second electrode structure, or a first electrode/a single layer having both hole injection and hole transport capabilities/an emission layer/an electron transport layer/an electron injection layer/a second electrode structure. Alternatively, the organic light-emitting device may have a first electrode/a hole transport layer/an emission layer/a single layer having both electron injection and electron transport capabilities/a second electrode structure, a first electrode/a hole injection layer/an emission layer/a single layer having both electron injection and electron transport capabilities/a second electrode structure, or a first electrode/a hole injection layer/a hole transport layer/an emission layer/a single layer having both electron injection and electron transport capabilities/a second electrode structure.

According to some embodiments of the present invention, the organic light-emitting device may be either a top-emission organic light-emitting device or a bottom-emission organic light-emitting device.

Hereinafter, a method of manufacturing an organic light-emitting device according to an embodiment of the present invention will be described with reference to FIG. 1. FIG. 1 illustrates a structure of an organic light-emitting device according to an embodiment of the present invention. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (ELL), and a second electrode (cathode).

First, a first electrode is formed on a substrate by using a deposition or sputtering method. The first electrode may be formed of a first electrode material having a high work function. The first electrode may constitute an anode or a cathode. The substrate may be a substrate conventionally used in organic light-emitting devices, and may include, for example, a glass substrate or a transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide ($SnO_2$), zinc oxide (ZnO), aluminum (Al), silver (Ag), and magnesium (Mg), which have excellent conductivity. The first electrode may be formed as a transparent or reflective electrode.

Next, the HIL may be formed on the first electrode using various methods, for example, by vacuum deposition, spin coating, casting, Langmuir-Blodgett (LB) deposition, or the like.

When the HIL is formed using vacuum deposition, the deposition conditions may vary according to a material that is used to form the HIL, and the structure and thermal characteristics of the HIL. For example, the deposition conditions may include a deposition temperature of about 100° C. to about 500° C., a vacuum pressure of about $10^{-8}$ to about $10^{-3}$ torr, and a deposition rate of about 0.01 to about 100 Å/sec.

When the HIL is formed using spin coating, the coating conditions may vary according to a material used to form the HIL, and the structure and thermal properties of the HIL. For example, the coating conditions may include a coating speed of about 2000 rpm to about 5000 rpm, and a thermal treatment of about 80° C. to about 200° C. The remained solvent after coating may be removed.

The HIL may be formed of any material that is commonly used to form a HIL. Examples of the material that can be used to form the HIL include a phthalocyanine compound such as copperphthalocyanine, 4,4',4"-tris (3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS), but are not limited thereto.

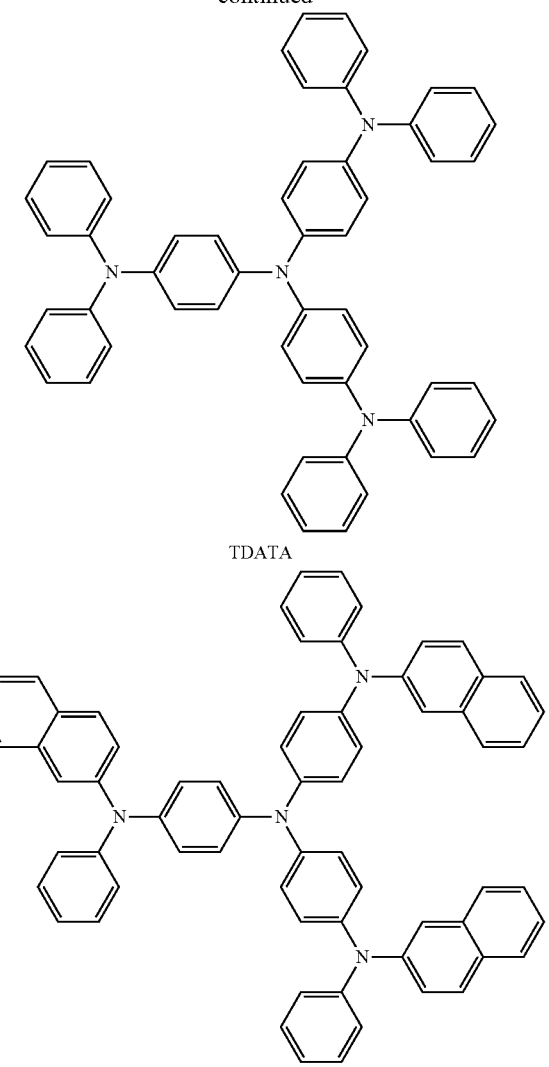

TDATA

2T-NATA

The HIL may have a thickness of about 100 Å to about 10000 Å, and in some other embodiments, may have a thickness of about 100 Å to about 1000 Å. When the thickness of the HIL is within these ranges, the HIL may have good hole injection characteristics without an increase in driving voltage.

Next, the HTL may be formed on the HIL using any of a variety of methods, for example, by vacuum deposition, spin coating, casting, Langmuir-Blodgett (LB) deposition, or the like. When the HTL is formed using vacuum deposition or spin coating, the deposition or coating conditions may be similar to those applied to form the HIL, though the deposition or coating conditions may vary according to the material that is used to form the HTL.

Alternatively, known HTL materials may be used. Examples of such HTL materials include, but are not limited to, carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD), or the like.

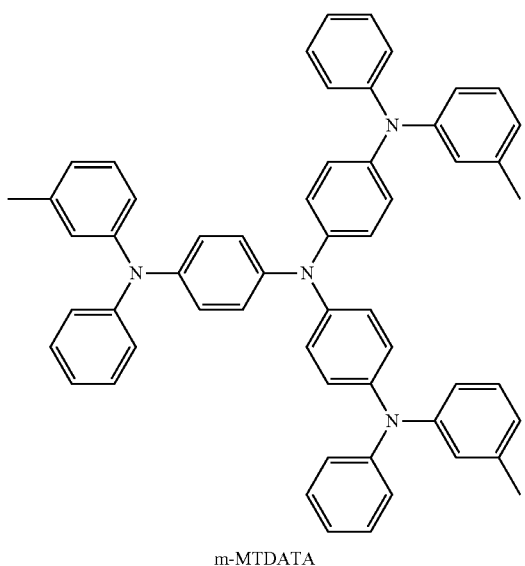

m-MTDATA

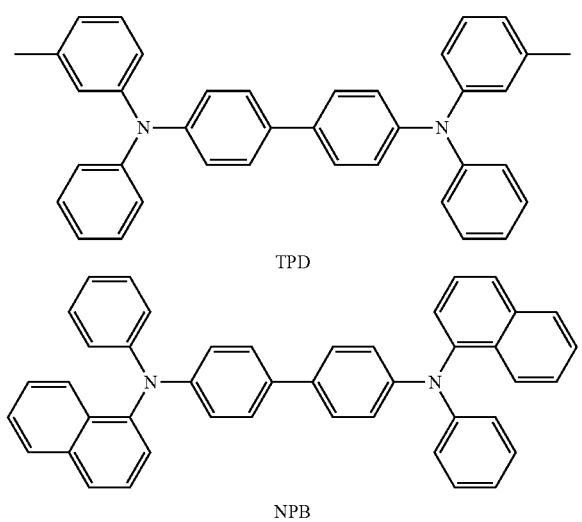

TPD

NPB

The HTL may have a thickness of about 50 Å to about 1000 Å, and in some embodiments, may have a thickness of about 100 Å to about 600 Å. When the thickness of the HTL is within these ranges, the HTL may have good hole transport characteristics without a substantial increase in driving voltage.

Next, the EML may be formed on the HTL using any of a variety of methods, for example, by vacuum deposition, spin coating, casting, LB deposition, or the like. When the EML is formed using vacuum deposition or spin coating, the deposition or coating condition may be similar to those applied to form the HIL, though the deposition or coating condition may vary according to the material that is used to form the EML.

The EML may be formed using any known light-emitting material, such as known hosts and dopants. Dopants that may be used to form the EML may include either a fluorescent dopant or a phosphorescent dopant which are widely known in the art.

Non-limiting examples of the hosts include Tris(8-hydroxyquinolinato)aluminium (Alq3), 4,4'-N,N'-dicarbazole-biphenyl (CBP), poly(n-vinylcarbazole) (PVK), 9,10-di(naphthalene-2-yl)anthracene (ADN), 1,3,5-tris(N-phenylbenzimidazole-2-yl)benzene (TPBI), 3-tert-butyl-9,10-di-2-naphthylanthracene (TBADN), E3, and distyrylarylene (DSA).

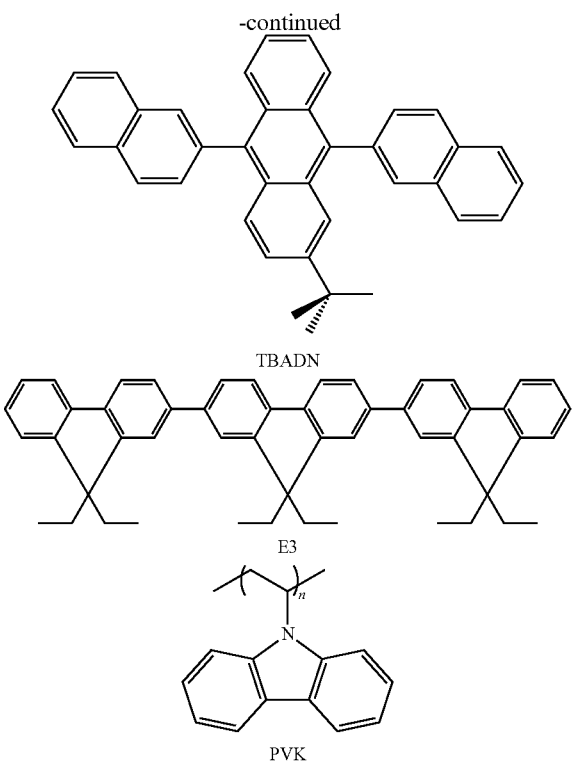

TBADN

E3

PVK

Examples of red dopants include, but are not limited to, platinum(II) octaethylporphyrin (PtOEP), Ir(piq)$_3$, Btp$_2$Ir(acac), and 4-(dicyanomethylene)-2-t-butyl-6(1,1,7,7-tetramethyljulolidyl-9-enyl)-4H-pyran (DCJTB).

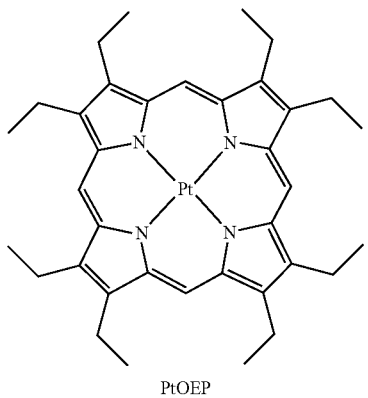

PtOEP

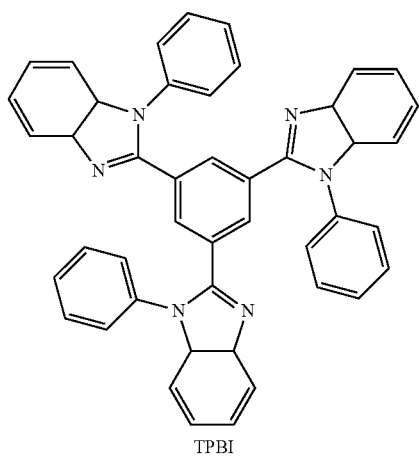

TPBI

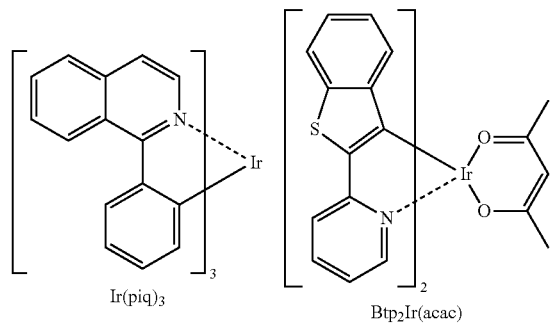

Ir(piq)$_3$

Btp$_2$Ir(acac)

Examples of green dopants may include, but are not limited to, Ir(ppy)₃ (where "ppy" denotes phenylpyridine), Ir(ppy)₂(acac), Ir(mpyp)₃, and C545T.
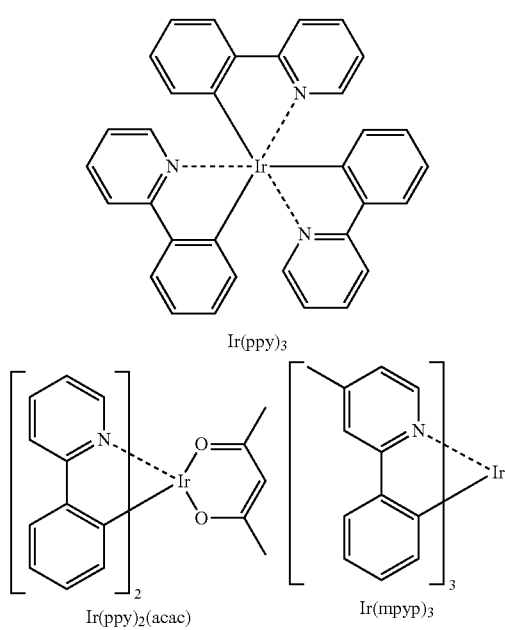
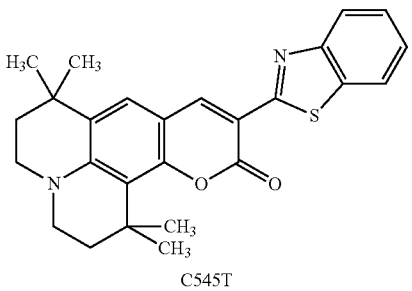
C545T
Examples of blue dopants include, but are not limited to, F₂Irpic, (F₂ppy)₂Ir(tmd), Ir(dfppz)₃, ter-fluorene 4,4'-bis(4-diphenylaminostyryl)biphenyl (DPAVBi), and 2,5,8,11-tetra-t-butyl pherylene (TBP).
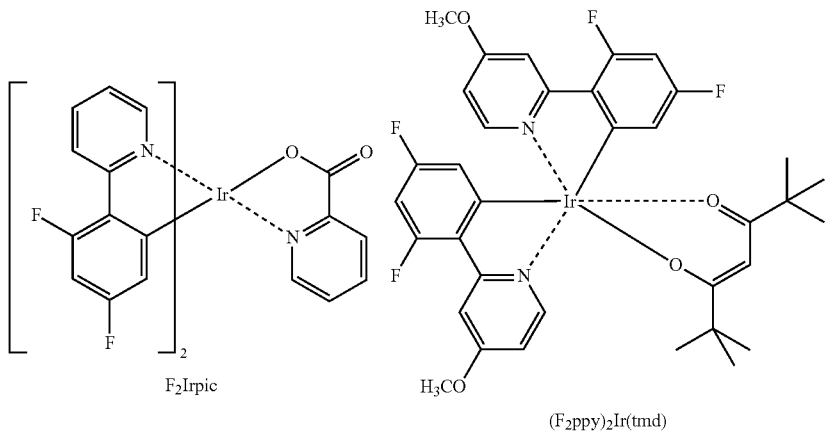
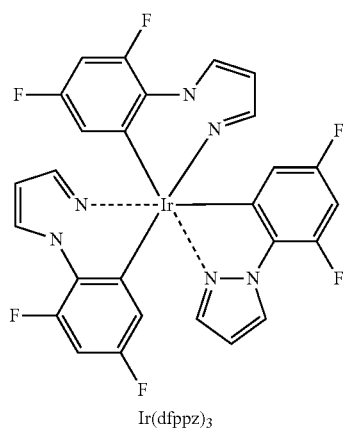
Ir(dfppz)₃

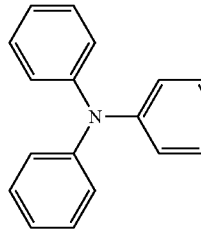
DPAVBi

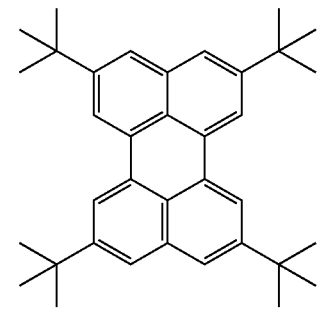
TBP

The amount of the dopants may be from about 0.1 to about 20 parts by weight, and in some other embodiments, may be from about 0.5 to about 12 parts by weight, based on 100 parts by weight of the EML material, which is equivalent to the total weight of the hosts and the dopants. When the amount of the dopants is within these ranges, concentration quenching may be substantially prevented.

The EML may have a thickness of about 100 Å to about 1,000 Å, and in some embodiments, may have a thickness of about 200 Å to about 600 Å. When the thickness of the EML is within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form a HBL. Examples of such HBL materials include, but are not limited to, oxadiazole derivatives, triazole derivatives, phenathroline derivatives, and Bis(2-methyl-8-quinolinolato-N1,O8)-(1,1'-Biphenyl-4-olato)aluminum (Balq).

The HBL may have a thickness of about 50 Å to about 1,000 Å, in some embodiments, may have a thickness of about 100 Å to about 300 Å. When the thickness of the HBL is within these ranges, the HBL may have good hole blocking characteristics without a substantial increase in driving voltage.

Next, the ETL is formed on the EML (or HBL) using various methods, for example, by vacuum deposition, spin coating, casting, or the like. When the ETL is formed using vacuum deposition or spin coating, the deposition or coating condition may be similar to those applied to form the HIL, though the deposition or coating condition may vary according to the material that is used to form the ETL.

The ETL material may include the heterocyclic compound of Formula 1 or Formula 2 described above. Alternatively, the ETL may be formed of any material that is widely known in the art. Examples of the ETL material include, but are not limited to, guillotine derivatives, such as tris(8-quinolinolate) aluminum (Alq3), TAZ, and BAlq.

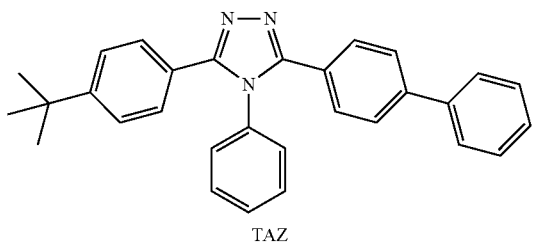
TAZ

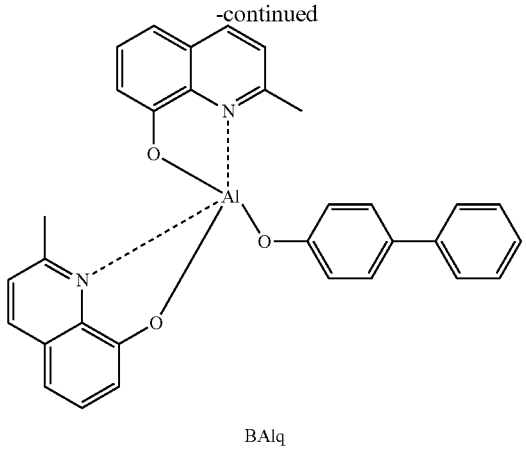
BAlq

The ETL may have a thickness of about 100 Å to about 1,000 Å, and in some other embodiments, may have a thickness of about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

The EIL is formed on the ETL using various methods, for example, by vacuum deposition, spin coating, casting, or the like. When the EIL is formed using vacuum deposition or spin coating, the deposition or coating condition may be similar to those applied to form the HIL, though the deposition or coating condition may vary according to the material that is used to form the EIL.

An EIL material may include the heterocyclic compound of Formula 1 or Formula 2 described above. Alternatively, well-known EIL materials, such as LiF, NaCl, CsF, $Li_2O$, or BaO, may be used to form the EIL.

The EIL may have a thickness of about 1 Å to about 100 Å, and in some other embodiments, may have a thickness of about 5 Å to about 90 Å. When the thickness of the EIL is within these ranges, the EIL may have good electron injection characteristics without a substantial increase in driving voltage.

Finally, the second electrode may be formed on the EIL by using, for example, vacuum deposition, sputtering, or the like. The second electrode may constitute a cathode or an anode. The material for forming the second electrode may include a metal, an alloy, or an electrically conductive compound, which are materials having a low work function, or a mixture thereof Examples of such materials include, but are not limited to, lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode formed of a transparent material such as ITO or IZO may be used as the second electrode.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organ c light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments, the organic light-emitting device may include an organic layer including a plurality of layers, wherein at least one of the layers may be formed of the heterocyclic compound of Formula 1 or Formula 2 by a deposition method or a wet method of coating a solution of the heterocyclic compound of Formula 1 or Formula 2.

Hereinafter, synthesis examples of Compounds 1, 3, 8, 11 and 13 and examples will be described in detail. However, these examples are presented for illustrative purposes only, and do not limit the scope of the present invention.

EXAMPLES

Synthesis Example 1

Synthesis of Compound 1

Compound 1 was synthesized according to Reaction Scheme 1 below:

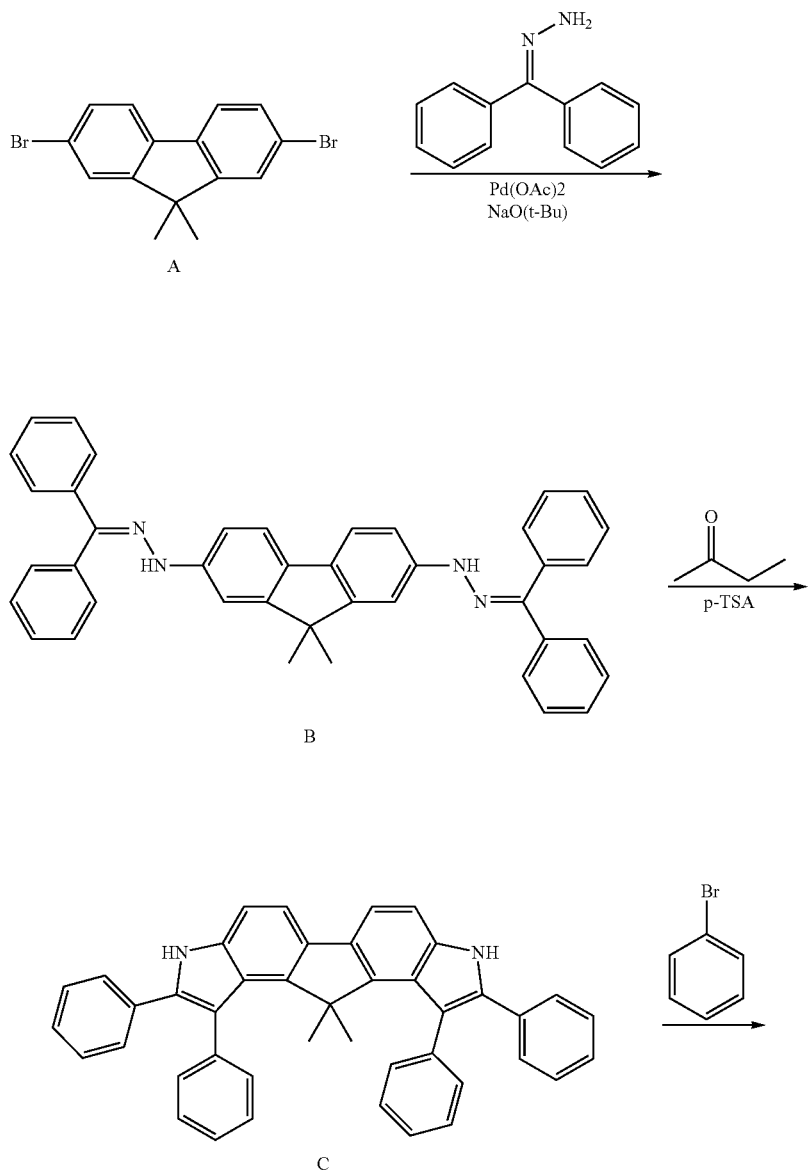

-continued

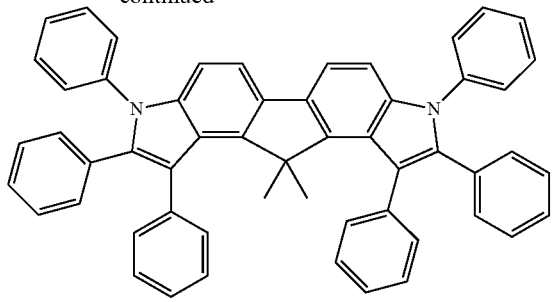

Compound 1

1) Synthesis of Intermediate B 0.1 mol (35.2 g) of Intermediate A, 0.22 mol (43.2 g) of diphenylmethylenchydrazine, 3.2 g of Pd$_2$(dba)$_3$, 700 mg of P(t-Bu)$_3$, and 25 g of NaOtBu were dissolved in 250 mL of xylene, and then were reacted at about 80° C. for about 12 hours. After completion of the reaction, the reaction mixture was cooled to room temperature and then extracted by adding 500 mL of distilled water in a volume ratio of xylene to water of 1:1. The organic phase was collected and then dried using MgSO$_4$, followed by concentration. The concentrated product was separated using silica gel column chromatography in which a 1:2 mixture of toluene and hexane (by volume) was used as an eluent. Then, the resulting eluent was concentrated and dried to obtain 29 g of Compound B with a yield of 50%. The produced compound was identified using NMR.

1H NMR (CDCl3, 400 MHz) δ(ppm) 7.97 (4H), 7.62-7.56 (18H), 6.75 (2H), 6.58 (2H), 1.72 (6H), 7.00 (NH).

2) Synthesis of Intermediate C 0.05 mol (29 g) of intermediate B, and 0.1 mol (17.2 g) of p-TSA were put into a flask, followed by an addition of 300 mL of methyl ethyl ketone as a catalyst and solvent. This mixture was refluxed for reaction for about 12 hours. After completion of the reaction, the reaction mixture was cooled to room temperature and then extracted by adding 500 mL of distilled water in a volume ratio of ethylacetate to water of 1:1. The organic phase was collected and then dried using MgSO$_4$, followed by concentration. The concentrated product was separated using silica gel column chromatography in which a 3:7 mixture of ethylacetate and hexane (by volume) was used as an eluent. Then, the resulting eluent was concentrated and dried to obtain 15 g of Compound C with a yield of 50%. The produced compound was identified using NMR.

1H NMR (CDCl3, 400 MHz) δ(ppm) 8.20 (2H), 7.80-7.70 (6H), 7.52-7.32 (18H), 1.72 (6H), 11.36 (NH).

3) Synthesis of Compound 1

0.02 mol (15 g) of Intermediate C, 0.04 mol (6.3 g) of bromoaniline, 0.045 mol (4.2 g) of t-BuONa, 0.54 g (0.6 mol) of Pd$_2$(dba)$_3$, and 0.12 g (0.6 mol) of P(t-Bu)$_3$ were dissolved in 120 ml of toluene, and then were agitated at about 90° C. for about 3 hours. After the reaction was completed, the reaction solution was cooled to room temperature, and then extracted three times with distilled water and 120 ml of diethylether. The organic phase was collected and dried over anhydrous magnesium sulfate, and the residual solvent was evaporated. The residue was isolated and separated by silica gel column chromatography to produce 11.4 g of Compound 1 with a yield of 78%. The produced compound was identified using NMR.

1H NMR (CDCl3, 400 MHz) δ(ppm) 8.20 (2H), 7.80 (4H), 7.60-7.40 (28H), 1.72 (8H).

Synthesis Example 2

Synthesis of Compound 3

Compound 3 was synthesized according to Reaction Scheme 2 below:

Reaction Scheme 2

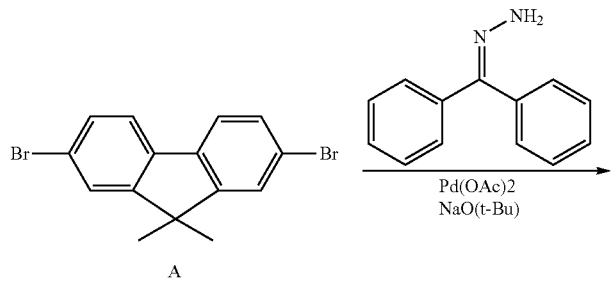

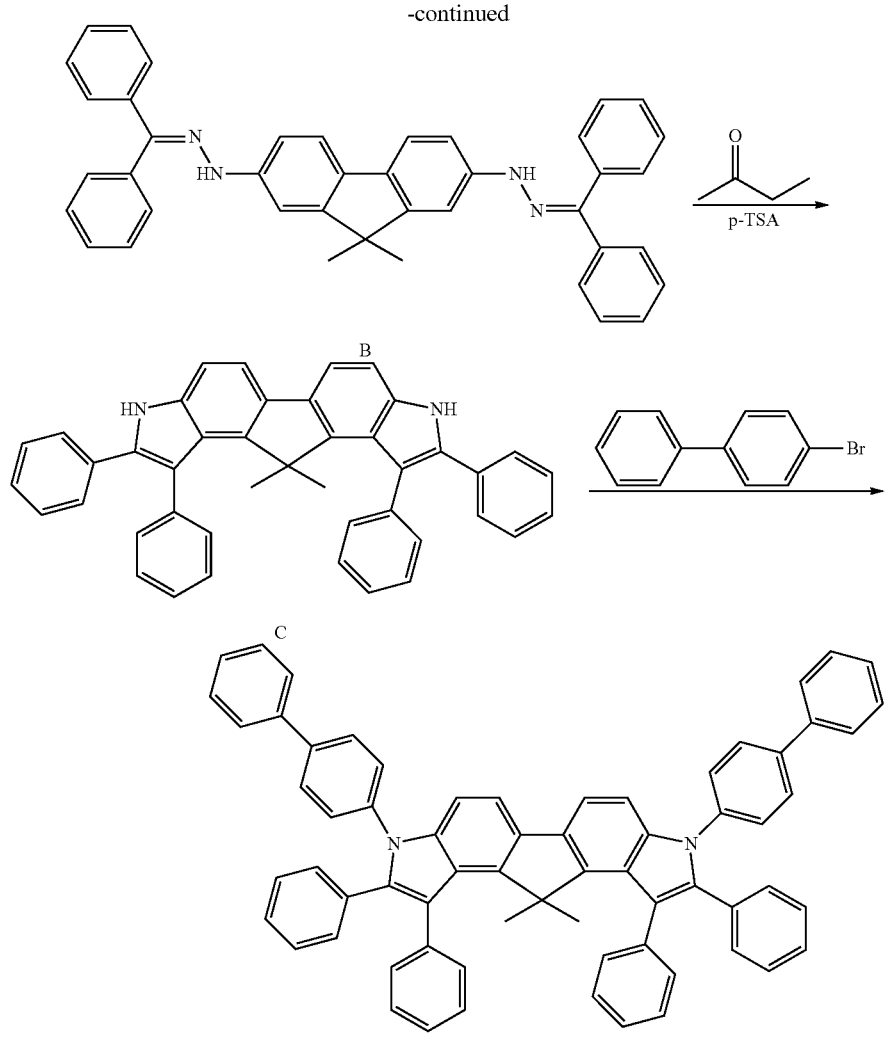

Compound 3

Compound 3 was synthesized in the same manner as in Synthesis Example 1, except that 4-bromo-1,1'-biphenyl was used instead of bromoaniline used in the synthesis of Compound 1. The produced compound was identified using NMR.

1H NMR (CDCl3, 400 MHz) δ(ppm) 8.20 (2H), 7.80 (8H), 7.69 (4H), 7.60-7.40 (28H), 1.72 (18H).

Synthesis Example 3

Synthesis of Compound 8

Compound 8 was synthesized according to Reaction Scheme 3 below:

Reaction Scheme 3

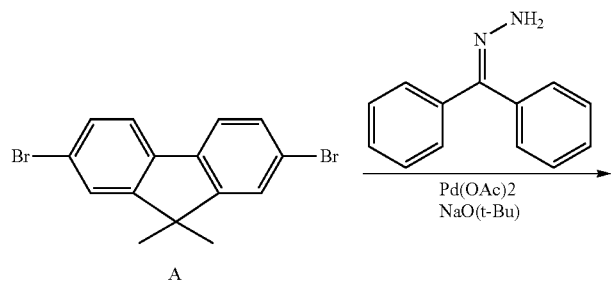

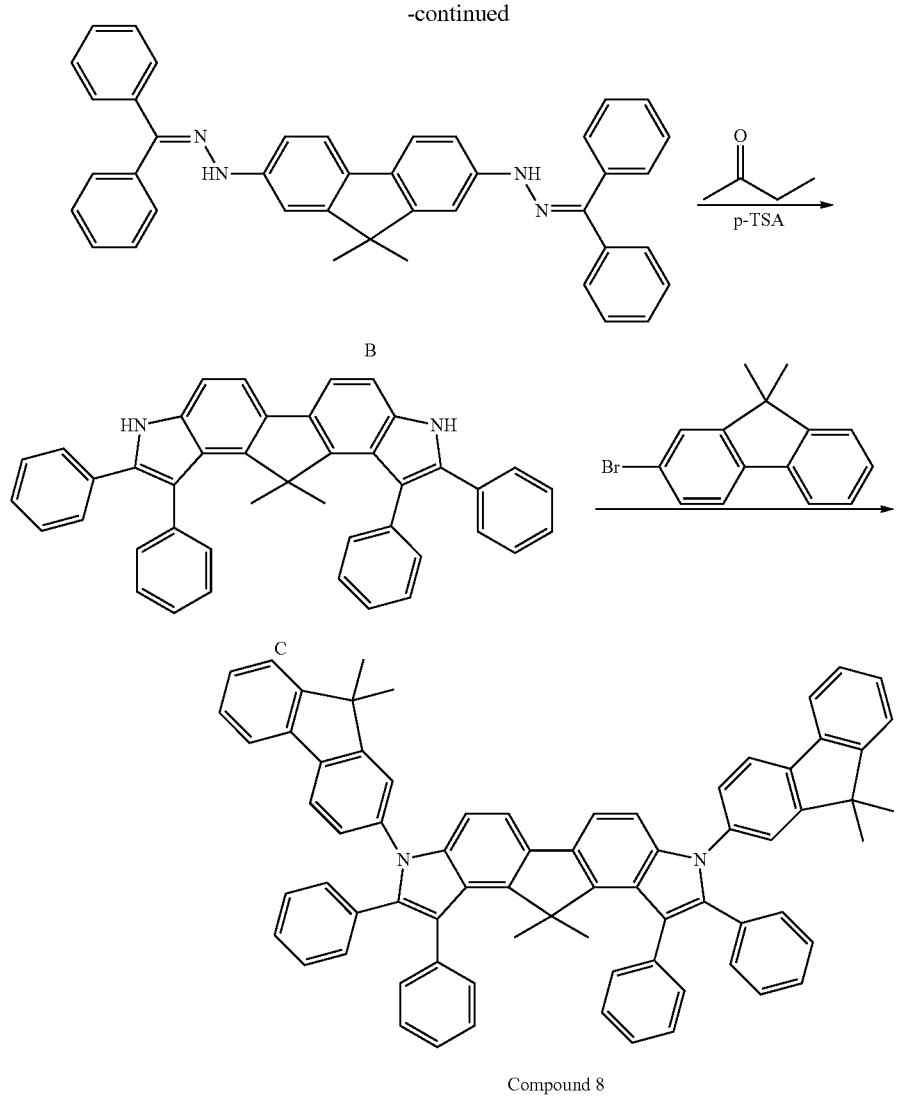

Compound 8

Compound 8 was synthesized in the same manner as in Synthesis Example 1, except that bromofluorene was used instead of bromoaniline used in the synthesis of Compound 1. The produced compound was identified using NMR.

1H NMR (CDCl3, 400 MHz) δ(ppm) 8.20 (2H), 7.86 (4H), 7.80 (4H), 7.59-7.34 (22H), 7.18-7.07 (6H), 1.72 (18H).

Synthesis Example 4

Synthesis of Compound 11

Compound 11 was synthesized according to Reaction Scheme 4 below:

Reaction Scheme 4

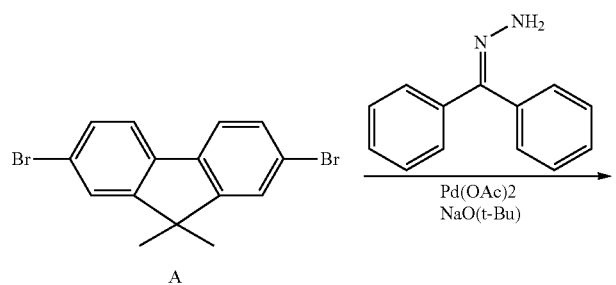

-continued

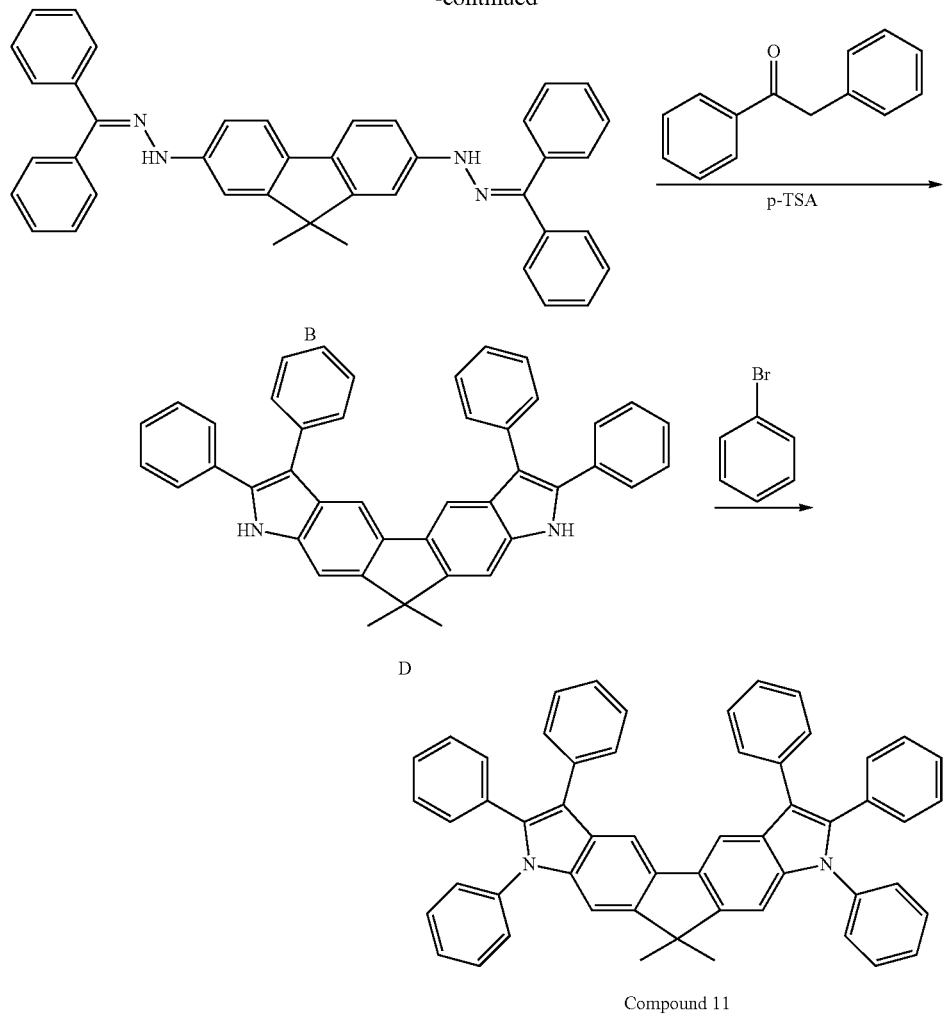

1) Synthesis of Intermediate D

Intermediate D was synthesized in the same manner as in Synthesis Example 1, except that 1,2-diphenylketone was used instead of methyl ethyl ketone used in the synthesis of intermediate C. The produced compound was identified using NMR.

1H NMR (CDCl3, 400 MHz) δ(ppm) 7.80 (4H), 7.40-7.50 (18H), 7.06 (2H), 1.72 (6H), 11.36 (NH).

2) Synthesis of Compound 11

Compound 11 was synthesized in the same manner as in Synthesis Example 1, except that Intermediate D was used instead of Intermediate C used in the synthesis of Compound 1. The produced compound was identified using NMR.

1H NMR (CDCl3, 400 MHz) δ(ppm) 8.16 (2H), 7.80-7.75 (6H), 7.59-7.42 (26H), 1.72 (6H).

Synthesis Example 5

Synthesis of Compound 13

Compound 13 was synthesized according to Reaction Scheme 5 below:

Reaction Scheme 5

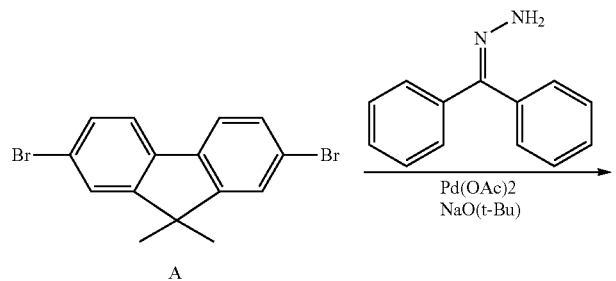

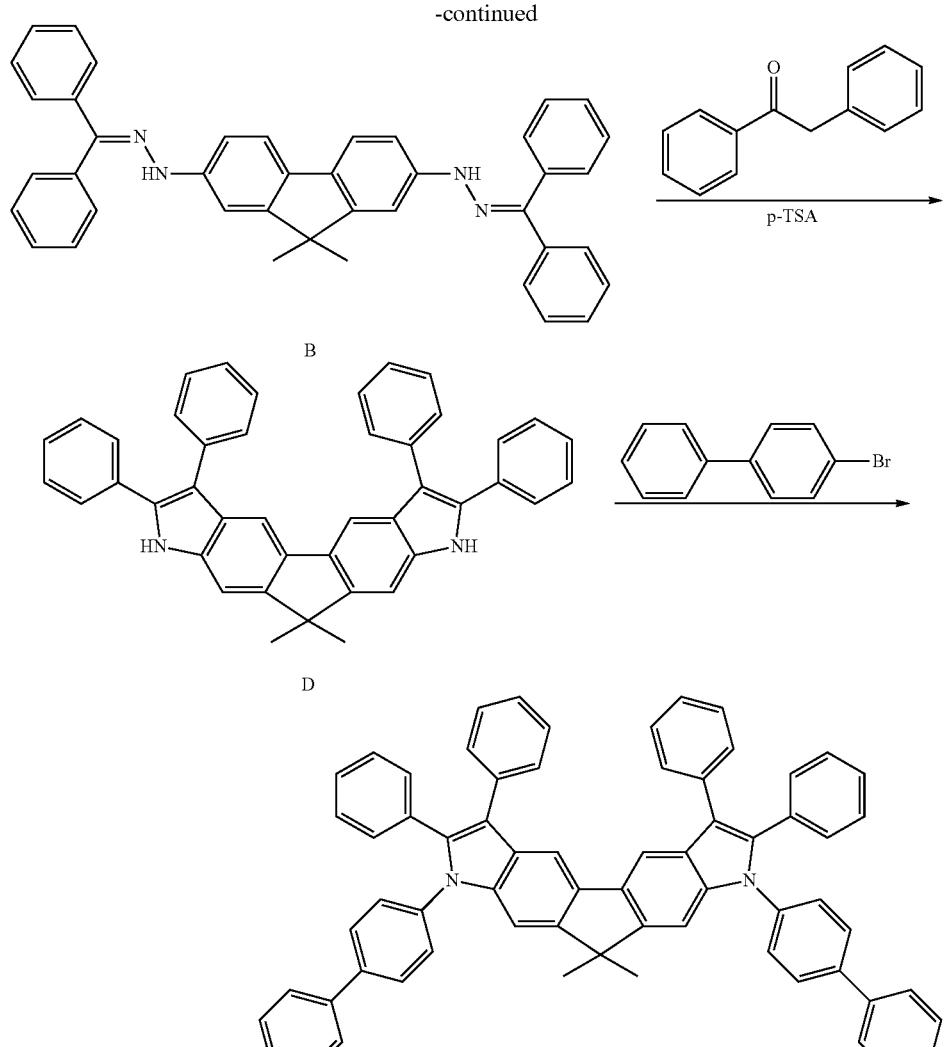

Compound 13

Compound 13 was synthesized in the same manner as in Synthesis Example 4, except that bromobiphenyl were used instead of bromoaniline used in the synthesis of Compound 11. The produced compound was identified using NMR.

1H NMR (CDCl3, 400 MHz) δ(ppm) 8.16 (2H), 7.79-7.74 (10H), 7.68 (4H), 7.52-7.41 (26H), 1.72 (6H).

Example 1

As an anode, a 15 Ω/cm² (1200 Å) ITO glass substrate (produced by Corning Co.) was cut to a size of 50 mm×50 mm×0.7 mm and then sonicated with isopropyl alcohol and pure water each for 5 minutes and washed by irradiation of ultraviolet rays for 30 minutes and exposure to ozone. Then, the resultant glass substrate was mounted on a vacuum deposition device. 2-TNATA was vacuum-deposited on the anode to a thickness of 600 Å to form an HIL, and α-NPD as a hole transporting compound was vacuum-deposited on the HIL to a thickness of 300 Å to form a HTL.

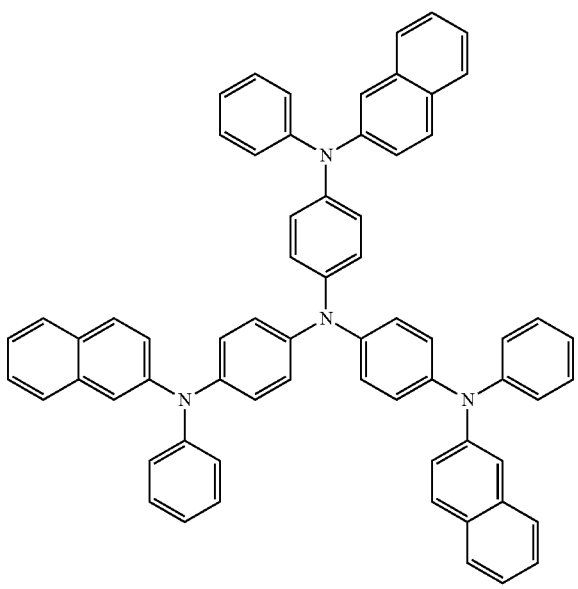

2-TNATA

IDE215 (Idemitsu Co.) as a known blue fluorescent host and IDE118 (Idemitsu Co.) as a known blue fluorescent dopant were co-deposited in a weight ratio of 98:2 on the HTL to form an EML having a thickness of 200 Å. Then, Compound 1 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

Example 2

An organic light-emitting device was manufactured in the same manner as in Example 1, except that Compound 3 was used instead of Compound 1 to form the ETL.

Example 3

An organic light-emitting device was manufactured in the same manner as in Example 1, except that Compound 8 was used instead of Compound 1 to form the ETL.

Example 4

An organic light-emitting device was manufactured in the same manner as in Example 1, except that Compound 11 was used instead of Compound 1 to form the ETL.

Example 5

An organic light-emitting device was manufactured in the same manner as in Example 1, except that Compound 13 was used instead of Compound 1 to form the ETL.

Comparative Example 1

An organic light-emitting device was manufactured in the same manner as in Example 1, except that Alq3, known as an electron transport material, was used, instead of Compound 1, to form the ETL.

For the organic light-emitting devices manufactured using the heterocyclic compound of Formula 1 or Formula 2 as an electron transport layer material, the driving voltage was lower, and the efficiency, I-V-L characteristics and lifetime improvement were better, as compared to when the widely-known material Alq3 was used. The characteristics of the organic light-emitting devices of Examples 1-5 and Comparative Example 1 are shown in Table 1 below.

The heterocyclic compounds according to embodiments of the present invention have good electrical characteristics and charge transporting capabilities, and thus may be used as an electron injecting material, an electron transporting material or an emitting material for most color-fluorescent and phosphorescent devices, such as red, green, blue, and white fluorescent and phosphorescent devices. Thus, an organic light-emitting device including an organic layer containing the heterocyclic compound of Formula 1 or Formula 2 may have high-efficiency, low driving voltage, and high luminance.

While the present invention has been particularly shown and described with reference to exemplary embodiments thereof, it will be understood by those of ordinary skill in the art that various changes in for and details may be made therein without departing from the spirit and scope of the present invention as defined by the following claims.

What is claimed is:

1. A heterocyclic compound represented by Formula 1 or Formula 2 below:

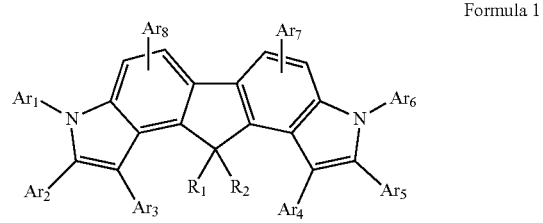

Formula 1 wherein, in Formula 1, $R_1$ and $R_2$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a halogen atom, a cyano group, a nitro group, a hydroxyl group, or a carboxyl group; and $Ar_1$ to $Ar_8$ are each independently a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_4$-$C_{60}$ heteroaryl group, a substituted or unsubstituted $C_4$-$C_{60}$ heteroaryl group, or a substituted or unsubstituted $C_6$-$C_{60}$ condensed polycyclic group, and

TABLE 1

|  | ETL material | Driving voltage (V) | Current density (mA/cm$^2$) | Luminescent efficiency (cd/A) | IS lifetime (h)(@700 nit) | Color coordinates |
| --- | --- | --- | --- | --- | --- | --- |
| Example 1 | Compound 1 | 7.1 | 100 | 7.4 | 30> | (0.143, 0.230) |
| Example 2 | Compound 3 | 6.8 | 100 | 7.8 | 40> | (0.144, 0.229) |
| Example 3 | Compound 8 | 6.9 | 100 | 8.1 | 40> | (0.143, 0.230) |
| Example 4 | Compound 11 | 7.2 | 100 | 7.6 | 30> | (0.143, 0.232) |
| Example 5 | Compound 13 | 6.8 | 100 | 8.8 | 30> | (0.145, 0.230) |
| Comparative Example 1 | Alq3 | 7.4 | 100 | 6.1 | 20 | (0.143, 0.232) |

Formula 2

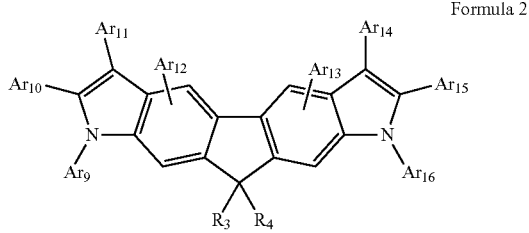

wherein, in Formula 2, $R_3$ and $R_4$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a halogen atom, a cyano group, a nitro group, a hydroxyl group, or a carboxyl group; and $Ar_9$ to $Ar_{16}$ are each independently a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_4$-$C_{60}$ heteroaryl group, a substituted or unsubstituted $C_4$-$C_{60}$ heteroaryl group, or a substituted or unsubstituted $C_6$-$C_{60}$ condensed polycyclic group.

2. The heterocyclic compound of claim 1, wherein $R_1$ to $R_4$ in Formulae 1 and 2 are each independently selected from the group consisting of a hydrogen atom, a deuterium atom, a halogen atom, a cyano group, and a substituted or unsubstituted $C_1$-$C_{20}$ alkyl group.

3. The heterocyclic compound of claim 1, wherein $Ar_1$ to $Ar_{16}$ are each independently selected from among groups represented by Formulae 2a to 2f below:

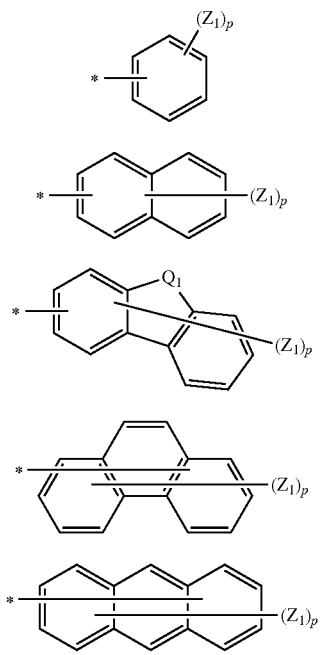

-continued

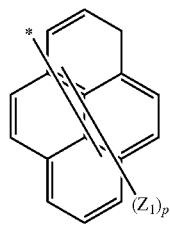

wherein, in Formulae 2a to 2f, $Q_1$ is a linking group represented by —$C(R_5)(R_6)$—, —$N(R_7)$—, —S—, or —O—;

$Z_1$, $R_5$, $R_6$, and $R_7$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 12; and

* indicates a binding site.

4. The heterocyclic compound of claim 1, wherein $R_1$ to $R_4$ in Formulae 1 and 2 are each independently selected from the group consisting of a hydrogen atom, a deuterium atom, a cyano group, a halogen atom, and a substituted or unsubstituted $C_1$-$C_{20}$ alkyl group; and $Ar_1$ to $Ar_{16}$ are each independently a substituted or unsubstituted $C_5$-$C_{30}$ aryl group, a substituted or unsubstituted $C_4$-$C_{30}$ heteroaryl group, or a substituted or unsubstituted $C_6$-$C_{30}$ condensed polycyclic group.

5. A heterocyclic compound represented by Formula 1 or Formula 2 below:

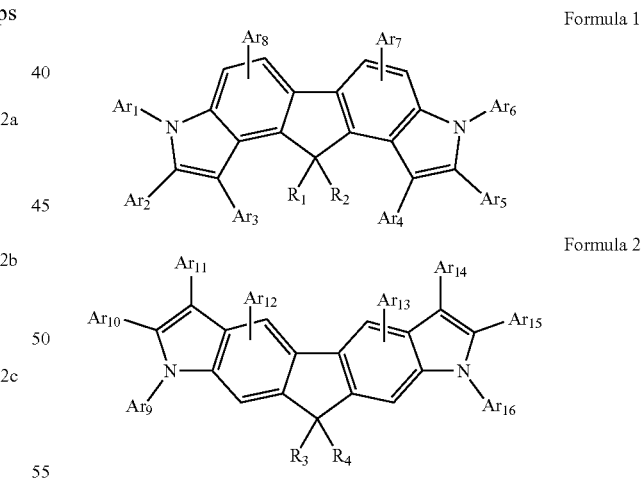

wherein in Formulae 1 and 2, $R_1$ to $R_4$ are substituted or unsubstituted $C_1$-$C_{20}$ alkyl groups; $Ar_7$, $Ar_8$, $Ar_{12}$, and $Ar_{13}$ are hydrogen atoms; and $Ar_1$ to $Ar_6$, $Ar_9$ to $Ar_{11}$, and $Ar_{14}$ to $Ar_{16}$ are each independently a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_4$-$C_{60}$ heteroaryl group, a substituted or unsubstituted $C_4$-$C_{60}$ heteroaryl group, or a substituted or unsubstituted $C_6$-$C_{60}$ condensed polycyclic group.

6. The heterocyclic compound of claim 5, wherein in Formulae 1 and 2, $R_1$ to $R_4$ are methyl groups, $Ar_7$, $Ar_8$, $Ar_{12}$, and $Ar_{13}$ are hydrogen atoms; and $Ar_1$ to $Ar_6$, $Ar_9$ to $Ar_{11}$, and $Ar_{14}$ to $Ar_{16}$ are each independently selected from among groups represented by Formulae 2a to 2f:

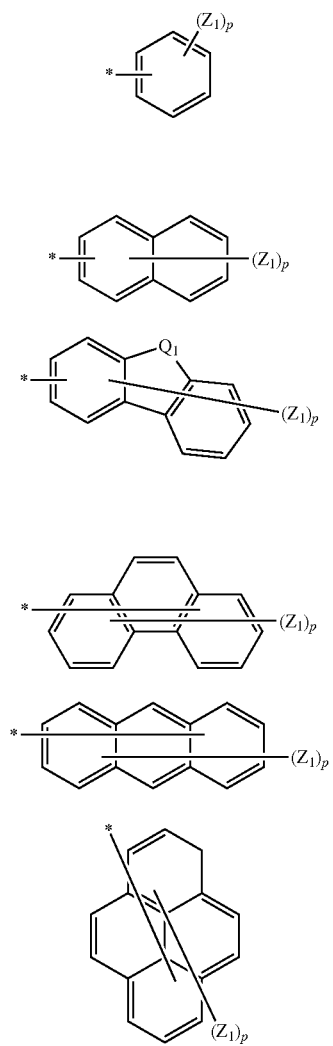

wherein in Formulae 2a to 2f, $Q_1$ is a linking group represented by —C($R_5$)($R_6$)—, —N($R_7$)—, —S—, or —O—;

$Z_1$, $R_5$, $R_6$, and $R_7$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 12; and

\* indicates a binding site.

7. The heterocyclic compound of claim 5, wherein the compound of Formula 1 or Formula 2 comprises one of the compounds below:

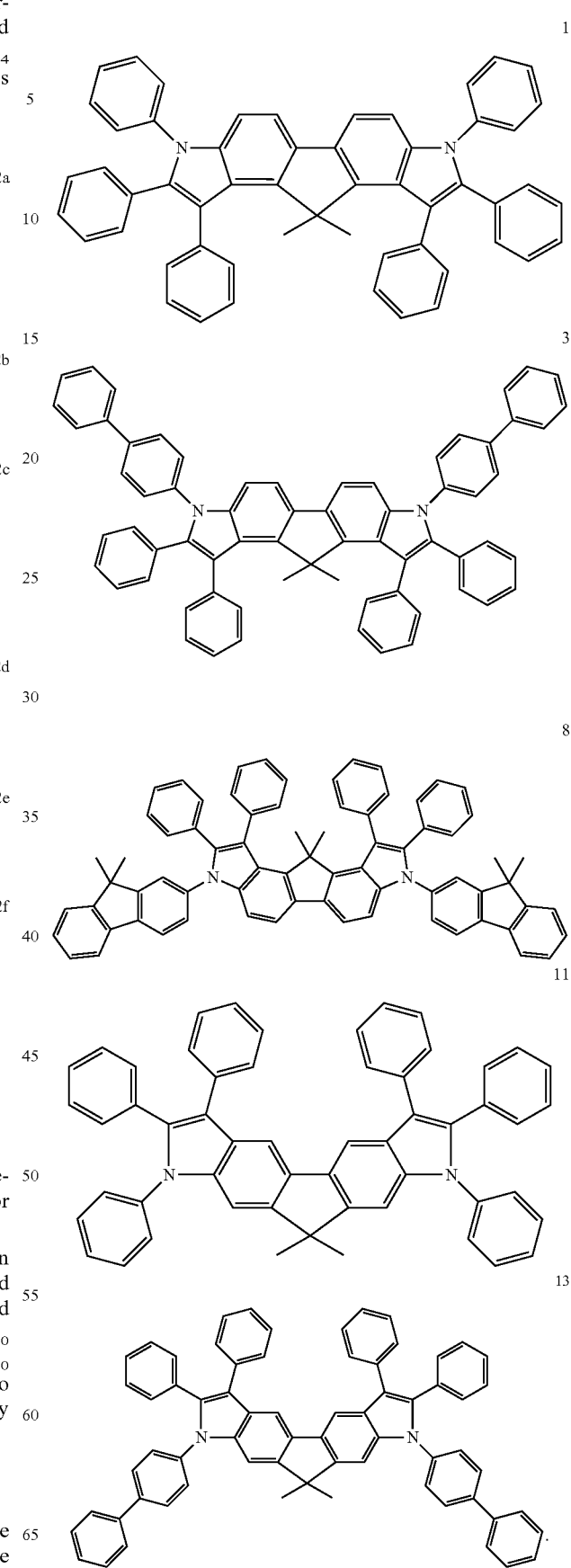

8. An organic light-emitting device comprising:
a first electrode;
a second electrode; and
an organic layer formed between the first electrode and the second electrode,
wherein the organic layer comprises the heterocyclic compound represented by Formula 1 or Formula 2 of claim 1.

9. The organic light-emitting device of claim 8, wherein the organic layer comprises a layer comprising the heterocyclic compound represented by Formula 1 or Formula 2 of claim 1.

10. The organic light-emitting device of claim 9, wherein the layer is an electron injection layer, an electron transport layer, or a single layer having hole injecting and transporting capabilities.

11. The organic light-emitting device of claim 8, wherein the organic layer comprises an emission layer, and an electron transport layer, wherein the electron transport layer comprises the heterocyclic compound of Formula 1 or Formula 2, and the emission layer comprises an anthracene compound, an arylamine compound, or a styryl compound.

12. The organic light-emitting device of claim 8, wherein the organic layer comprises an emission layer, and an electron transport layer, wherein the electron transport layer comprises the heterocyclic compound of Formula 1 or Formula 2, and the emission layer comprises red, green, blue, and white emission layers; and one of the red, green, blue, and white emission layers comprises a phosphorescent compound.

13. The organic light-emitting device of claim 8, wherein the organic layer comprises a hole injection layer, a hole transport layer, a functional layer having both hole injection and hole transport capabilities, an emission layer, a hole blocking layer, an electron transport layer, an electron injection layer, or a combination of at least two of the hole injection layer, the hole transport layer, the functional layer having both hole injection and hole transport capabilities, the emission layer, the hole blocking layer, the electron transport layer, and the electron injection layer thereof.

14. The organic light-emitting device of claim 13, wherein at least one of the hole injection layer, the hole transport layer, and the functional layer having hole injection and hole transport capabilities comprises a charge generating material.

15. The organic light-emitting device of claim 13, wherein the electron transport layer comprises an electron-transporting organic compound and a metal-containing compound.

16. The organic light-emitting device of claim 15, wherein the metal-containing compound comprises a lithium (Li) complex.

17. The organic light-emitting device of claim 9, wherein the layer is formed using a wet process.

18. A flat panel display device comprising the organic light-emitting device of claim 8, wherein the first electrode of the organic light-emitting device is electrically connected to a source electrode or a drain electrode of a thin-film transistor.

19. An organic light-emitting device comprising:
a first electrode;
a second electrode; and
an organic layer formed between the first electrode and the second electrode,
wherein the organic layer comprises the heterocyclic compound represented by Formula 1 or Formula 2 of claim 5.

* * * * *